(12) United States Patent
Brautaset et al.

US008859244B2

(10) Patent No.: US 8,859,244 B2
(45) Date of Patent: Oct. 14, 2014

(54) METHOD OF L-LYSINE PRODUCTION

(75) Inventors: Trygve Brautaset, Trondheim (NO);
Øyvind Mejdell Jakobsen, Trondheim (NO); Trond Ellingsen, Ranheim (NO)

(73) Assignee: Sinvent AS, Trondheim (NO)

( * ) Notice: Subject to any disclaimer, the term of this patent is extended or adjusted under 35 U.S.C. 154(b) by 505 days.

(21) Appl. No.: 12/993,399

(22) PCT Filed: May 15, 2009

(86) PCT No.: PCT/GB2009/001265
§ 371 (c)(1),
(2), (4) Date: Mar. 14, 2011

(87) PCT Pub. No.: WO2009/141607
PCT Pub. Date: Nov. 26, 2009

(65) Prior Publication Data
US 2011/0177568 A1 Jul. 21, 2011

(30) Foreign Application Priority Data
May 20, 2008 (GB) .................................. 0809169.6

(51) Int. Cl.
*C12P 13/08* (2006.01)
*C12N 9/00* (2006.01)
*C12N 9/12* (2006.01)
*C12N 1/20* (2006.01)
*C12N 15/00* (2006.01)
*C07H 21/04* (2006.01)
*C12N 1/32* (2006.01)

(52) U.S. Cl.
CPC ............... *C12N 9/1217* (2013.01); *C12P 13/08* (2013.01); *C12N 1/32* (2013.01)
USPC ........ 435/115; 435/183; 435/194; 435/252.3; 435/320.1; 536/23.2

(58) Field of Classification Search
None
See application file for complete search history.

(56) References Cited

U.S. PATENT DOCUMENTS

| 5,243,039 A | 9/1993 | Schendel et al. |
| 5,426,052 A | 6/1995 | Flickinger et al. |
| 6,083,728 A | 7/2000 | Schendel et al. |
| 6,110,713 A | 8/2000 | Hanson et al. |
| 6,201,825 B1 | 3/2001 | Sakurai et al. |
| 2009/0239269 A1 | 9/2009 | Tajima et al. |

FOREIGN PATENT DOCUMENTS

| EP | 0837134 A2 | 4/1998 |
| EP | 1063288 A1 | 12/2000 |
| JP | 2001-057896 A | 3/2001 |
| WO | 2008/044453 A1 | 4/2008 |
| WO | 2008/092956 A1 | 8/2008 |

OTHER PUBLICATIONS

Accession Q2B0K5, Apr. 4, 2006.*
Chica et al. Curr Opin Biotechnol. Aug. 2005;16(4):378-84.*
Sen et al. Appl Biochem Biotechnol. Dec. 2007;143(3):212-23.*
Jakobsen et al, Applied and Environmental Microbiology, 75(3):652-661 (Feb. 2009).
Huang et al, Proceedings of the National Science Council Republic of China Part B Life Sciences, 17(3):91-97 (1993).
Brautaset et al, Applied Microbiology and Biotechnology, Springer, Berlin, Germany, 74(1):22-34 (Jan. 11, 2007).
Schendel et al, Applied and Environmental Microbiology, 58(9):2806-2814 (1992).
Database Uniport: Q2B0K5 dated Apr. 4, 2006.
Database Uniport: Q65NE6 dated Oct. 25, 2004.
Kobashi et al, Bioscience Biotechnology Biochemistry, Japan Society for Bioscience, Biotechnology, and Agrochemistry, Tokyo, Japan, 65(6):1391-1394.
Ikeda, "Amino Acid Production Processes", Advances in Biochemical Engineering/Biotechnology, vol. 79, Faurie et al (Eds.), Springer-Verlag Berlin Heidelberg, pp. 1-35 (2003).
Marx et al, "Protein Line and Amino Acid-based Product Family Trees", Biorefineries—Industrial Processes and Products, Status Quo and Future Directions, Kamm et al (Eds.), Wiley-VCH Berlag GmbH & Co., pp. 201-216 (2006).
Kelle et al, "L-Lysine Production", Handbook of Corynebacterium glutamicum, Eggeling et al (Eds.), Taylor and Francis, pp. 465-488 (2005).
Linton et al, The Potential of One-Carbon Compounds as Fermentation Feedstocks, Antonie Van Leeuwenhoek, (1987) 53:55-63.
Izumi et al, L-Serine Production by a Methylotroph and its Related Enzymes, Applied Microbiology and Biotechnology (1993) 39:427-432.
Hagishita et al, Efficient L-Serine Production from Methanol and Glycine by Resting Cells of Methylobacterium sp. Strain MN43, Bioscience Biotechnology Biochemistry, 60(10):1604-1607 (1996).

(Continued)

*Primary Examiner* — Christian Fronda
(74) *Attorney, Agent, or Firm* — Porter Wright Morris & Arthur LLP

(57) ABSTRACT

The present invention relates to a method of microbial production of L-lysine from methanol and other substrates, and particularly improving the production of L-lysine from such substrates. The invention concerns a method for producing L-lysine in *B. methanolicus*, said method comprising overexpressing an aspartate kinase III (AKIII) enzyme in said *B. methanolicus*. In particular the method may concern introducing a nucleic acid molecule comprising a nucleotide sequence encoding an AKIII enzyme into a *B. methanolicus*. The invention also relates to a *B. methanolicus* micro-organism which overexpresses an AKIII enzyme, nucleic acid molecules which encode polypeptides having AK activity, polypeptides which have AK activity and host cells and vector systems comprising the nucleic acid molecules or vector.

31 Claims, 3 Drawing Sheets

(56) References Cited

OTHER PUBLICATIONS

Figure 1:
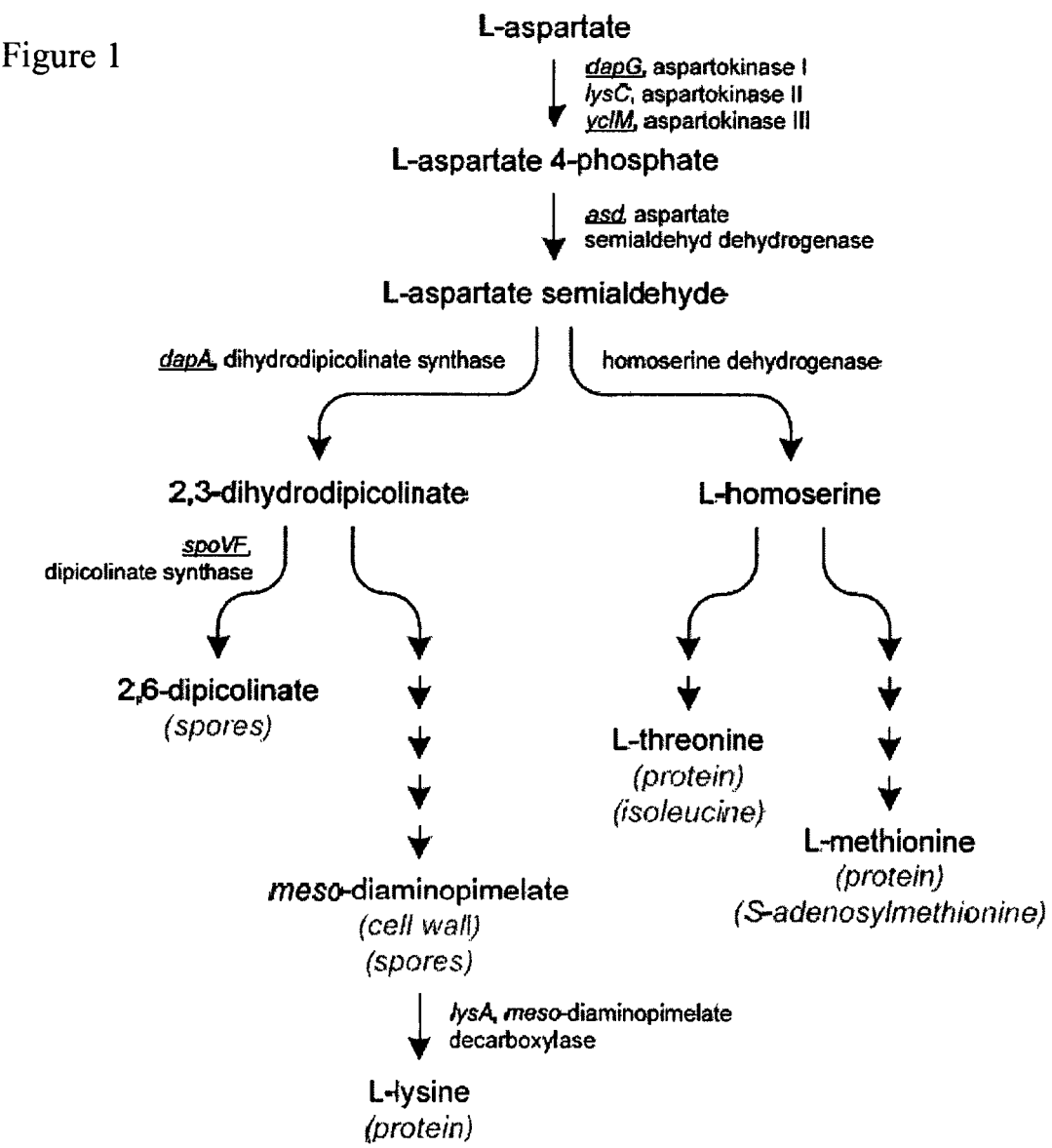

Motoyama et al, Effects of the Amplification of the genes coding for the L-threonine biosynthetic enzymes on the L-threonine production from methanol by a gram-negative obligate methylotroph, *Methylobacillus glycogenes*, Applied Microbiology and Biotechnology (1994) 42:67-72.

Motoyama et al, Amino Acid Production from Methanol by *Methylobacillus glycogenes* Mutants: Isolation of L-Glutamic Acid Hyper-producing Mutants from *M.glycogenes* Strains, and Derivation of L-Threonine and L-Lysine-producing Mutants from Them, Bioscience Biotechnology Biochemistry, 57 (1):82-87 (1993).

Motoyama et al, Overproduction of L-Lysine from Methanol by *Methylobacillus glycogenes* Derivatives Carrying a Plasmid with a Mutated dapA Gene, Applied and Environmental Microbiology, (2001), pp. 3064-3070.

Tsujimoto et al, L-Lysine biosynthetic pathway of Methylophilus methylotrophus and construction of an L-lysine producer, Journal of Biotechnology 124 (2006) 327-337.

Gunji et al, Enhancement of L-lysine production in methylotroph Methylophilus methylotrophus by introducing a mutant LysE exporter, Journal of Biotechnology 127(1):1-13 (2006).

Schendel, et al, L-Lysine Production at 50° C. by Mutants of a Newly Isolated and Characterized *Methylotrophic bacillus* sp., Applied and Environmental Microbiology, 56(4):963-970 (1990).

Pfefferle et al, "Biotechnological Manufacture of Lysine", Advances in Biochemical Engineering/Biotechnology, vol. 79, Faurie et al (Eds.), Springer-Verlag Berlin Heidelberg, pp. 59-85 (2003).

Ohnishi et al, A novel methodology employing *Corynebacterium glutamicum* genome information to generate a new L-lysine producing mutant, Appl Microbiology Biotechnology (2002) 58:217-223.

Jakobsen et al, Upregulated Transcription of Plasmid and Chromosomal Ribulose Monophosphate Pathway Genes is Critical for Methanol Assimilation Rate and Methanol Tolerance in the Methylotrophic Bacterium Bacillus methanolicus, Journal of Bacteriology, 188(8):3063-3072 (2006).

Cremer et al, Control of the Lysine Biosynthesis Sequence in *Corynebacterium glutamicum* as Analyzed by Overexpression of the Individual Corresponding Genes, Allied and Environmental Microbiology, 57(6):1746-1752 (1991).

Jetten et al, Effect of different levels of aspartokinase on the lysine production by *Corynebacterium* lactofermentum, Applied Microbiology and Biotechnology (1995), 43(1):76-82.

Zhang et al, Desensitization of *Bacillus subtilis* Aspartokinase I to Allosteric Inhibition by meso-Diaminopimelate Allows Aspartokinase I to Function in Amino Acid Biosynthesis during Exponential Growth, Journal of Bacteriology, 172 (8):4690-4693 (1990).

Vold et al, Regulation of Dihydrodipicolinate Synthase and Aspartate Kinase in *Bacillus subtilis*, Journal of Bacteriology, 121(3):970-974 (1975).

Koffas et al, Engineering metabolism and product formation in *Corynebacterium glutamicum* by coordinated gene overexpression, Metabolic Engineering 5(1):32-41 (2003).

Lu et al, Molecular Breeding of a *Brevibacterium* Flavum L-Lysine Producer Using a Cloned Aspartokinase Gene, Biotechnology Letters, vol. 16, No. 5 (1994), pp. 449-454.

Hua et al, Metabolic Control Analysis for Lysine Synthesis Using *Corynebacterium glutamicum* and Experimental Verification, Journal of Bioscience and Bioengineering, (2000) vol. 90, No. 2, pp. 184-192.

Mattioli et al, Characterization of Mutants of *Bacillus subtilis* Resistant to S-(2-Aminoethyl)cysteine, Journal of General Microbiology, (1979), 114, pp. 223-225.

Kunst et al, The Complete genome sequence of the Gram-positive bacterium *Bacillus subtillis*, Nature, vol. 390, (1997), pp. 249-256 and Table.

Rey et al, Complete genome sequence of the industrial bacterium *Bacillus licheniformis* and comparisons with closely related *Bacillus* species, Genome Biology, (2004), 5:R77.1-R77.12.

Takami et al, Complete genome sequence of the alkaliphilic bacterium *Bacillus halodurans* and genomic sequence comparison with *Bacillus subtilis*, Nucleic Acids Research, (2000), vol. 28, No. 21, p. 4317-4331.

Chen et al, Comparative analysis of the complete genome sequence of the plant growth-promoting bacterium *Bacillus amyloliquefaciens* FZB42, Nature Biotechnology, (2007), vol. 25, No. 9, 1007-1014.

Glaser et al, Comparative Genomics of *Listeria* Species, Science, vol. 294, (2001) p. 849-852.

Brautaset et al, Plasmid-Dependent Methylotrophy in Thermotolerant *Bacillus methanolicus*, Journal of Bacteriology (2004), vol. 186, No. 5, p. 1229-1238.

Hanson et al, "Production of L-Lysine and Some Other Amino Acids by Mutants of *B. methanolicus*", Microbial Growth on C1 Compounds, Lidstrom et al (Eds.), Kluwer Academic Publishers, Dordrecht, The Netherlands (2006), p. 227-236.

Black, et al, β-Aspartokinase and β-Aspartyl Phosphate, J. Biol. Chem., (2011), 213:27-38.

Cue et al, Genetic Manipulation of *Bacillus methanolicus*, a Gram-Positive, Thermotolerant Methylotroph, Applied and Environmental Microbiology, 63(4)1406-1420 (1997).

Thompson et al, Clustal W: improving the sensitivity of progressive multiple sequence alignment through sequence weighting, position-specific gap penalties and weight matrix choice, Nucleic Acids Research (1994), vol. 22, No. 22, 4673-4680.

Myers et al, Optimal alignments in linear space, CABIOS, (1988), 4:11-17.

Pearson et al, Improved Tools for Biological Sequence Comparison, Proceedings of the National Academy of Sciences, (1988) vol., 85, p. 2444-2448.

Altschul et al, Gapped BLAST and PSI-BLAST: a new generation of protein database search programs, Nucleic Acids Research (1997), vol. 25, No. 17, 3389-3402.

Holm et al, Protein Structure Comparison by Alignment of Distance Matrices, Journal of Molecular Biology (1993), vol. 233, p. 123-138.

Holm et al, Dali: a network tool for protein structure comparison, Trends in Biochemistry (1995), vol. 20, p. 478-480.

Holm et al, Touring protein fold space with Dali/FSSP, Nucleic Acids Research (1998), vol. 26, No. 1, p. 316-319.

Paulus, "Biosynthesis of the Aspartate Family of Amino Acids", *Bacillus subtilis* and other gram-positive bacteria: biochemistry, physiology and molecular genetics, Sonenshein (ed.), American Society for Microbiology (1993), pp. 237-267.

Skjerdal et al, Changes in intracellular composition in response to hyperosmotic stress of NaCl, sucrose or glutamic acid in *Brevibacterium* lactofermentum and *Corynebacterium glutamicum*, Applied Microbiology and Biotechnology, (1996), 44(5):635-642.

Brautaset et al, Role of the *Bacillus* methanolicus Citrate Synthase II Gene, CitY, in Regulating the Secretion of Glutamate in L-Lysine-Secreting Mutants, Applied and Environmental Microbiology, (2003), vol. 69, No. 7, p. 3986-3995.

Kobashi et al, Characterization of Aspartate Kinase II of *Bacillus subtilis*, Bioscience Biotechnology Biochemistry, (2001), vol. 65, No. 6, p. 1391-1394.

Chen et al, Organization and Nucleotide Sequence of the *Bacillus subtilis* Diaminopimelate Operon, a Cluster of Genes Encoding the First Three Enzymes of Diaminopimelate Synthesis and Dipicolinate Synthase, Journal of Biological Chemistry (1993), vol. 268, No. 13, p. 9448-9465.

Hollenberg et al, Production of Recombinant Proteins by Methylotrophic Yeasts, Current Opinion in Biotechnology, (1997), 8(5): 554-560.

Graves et al, Aspartokinase III, a New Isozyme in *Bacillus subtilis* 168, Journal of Bacteriology, (1990), 172 (1):218-221.

Jetten et al, Effect of different levels of aspartokinase on the lysine production by *Corynebacterium* lactofermentum, Applied Microbiology and Biotechnology (1995) 43(1):76-82.

Kato et al, Conversion of feedback regulation in aspartate kinase by domain exchange, Biochemical and Biophysical Research Communications (2004), 316(3):802-808.

(56) References Cited

OTHER PUBLICATIONS

Lee et al, Lysine Production from Methanol at 50° C. Using *Bacillus methanolicus*: Modeling Volume Control, Lysine Concentration, and Productivity Using a Three-Phase Continuous Simulation, Biotechnology and Bioengineering, (1996),. 49(6):639-653.

Lu et al, Identification of aecA mutations in *Bacillus subtilis* as nucleotide substitutions in the untranslated leader region of the aspartokinase II operon, Journal of General Microbiology (1991), 137:1135-1143.

Mills et al, Cloning and Sequence Analysis of the meso-Diaminopimelate Decarboxylase Gene from *Bacillus methanolicus* MGA3 and Comparison to Other Decarboxylase Genes, Applied and Environmental Microbiology, (1993), vol. 59, No. 9, p. 2927-2937.

Moir et al, Properties and Subunit Structure of Aspartokinase II from *Bacillus subtilis* VB217*, The Journal of Biological Chemistry, (1977), vol. 252, No. 13, p. 4648-4654.

Eggeling et al, Improved L-lysine yield with *Corynebacterium glutamicum*: use of dapA resulting in increased flux combined with growth limitation, Applied Microbiology and Biotechnology (1998), 49(1):24-30.

Rosner et al, Regulation of Aspartokinase in *Bacillus subtilis*, The Journal of Biological Chemistry, (1971), vol. 246, No. 9, p. 2965-2971.

UniProt Accession No. Q9KCR9 (2008).
UniProt Accession No. A7Z1C7 (2008).
UniProt Accession No. Q928Q9 (2008).
GenBank Accession No. CAB13549 (2006).
GenBank Accession No. BAB6119 (2007).
GenBank Accession No. AAU40796 (2007).
Frankard et al, Plant Mol. Biol., 34:233-242 (1997).
Official Action from corresponding Japanese Application No. 2011-510043 dated Jan. 14, 2014, including English translation.

* cited by examiner

SEQUENCE LISTING

```
<160> NUMBER OF SEQ ID NOS: 35

<210> SEQ ID NO 1
<211> LENGTH: 1242
<212> TYPE: DNA
<213> ORGANISM: Bacillus methanolicus

<400> SEQUENCE: 1
atgaaaatta tcgttcaaaa attcggggc  acttcggtcc gtgacgatat tagccgatcg    60
aatgcaaaaa ggcatataga aaaagctcta gccgaaggct acaaggttgt agttgttgta   120
tcagcgatgg gacgaagcgg tgaaccgtat gcaaccgata ccctcttatc gctaattgga   180
ggcaatgcga cgaaggtaag taaacgggag caagatttgc ttctttcttg cggagaaatc   240
atctcaagca ttgtttttac aaacatgctt attgagcatg gcattcgcgc tgttgcttta   300
accggtgccc aagcgggttt tcggacaaac aacgatcata cgaatgcaaa aattattgaa   360
atgaaatgcg acaggctttt aagggaattg aacaaaacg  aagttgtagt tgtagccggt   420
ttccaaggtg ctgcaaagaa tggcgatata acgaccattg gacgtggtgg cagcgataca   480
tcagccgctg ctttaggtgc agcgcttaat gctgaatgga ttgacatctt tactgatgtt   540
gagggaataa tgacagctga ccctcgaatt gttgagaatg cgcgtccttt atcggtagtc   600
acttacacgg aagtgtgcaa tatggcctat cagggtgcaa aggttataca ccctcgggcc   660
gtagaaatag caatgcaggc aaaaattccg atcaggattc gatcaactta ttcggacagc   720
cccggcacct tagttacctc actcagcaaa aatagtcgag gaagcgatat tcgagaacgg   780
ccggtaactg gaattgccca cgttccaaat gttacccaga ttaaagtttt cgctaaaaaa   840
```

```
gatcagtata atttacaagc tgaagtattt aaagcaatgg caaacgaaaa aatcagtgtt    900
gatttgataa atatatcgcc aaatggggtc gtttatacgg tgatgaatga aatggcagac    960
caagccattc gaattttgac cgatatggga catgagccgg ttgttgaacg ggattgtgca   1020
aaggtatccg ttgtcggtgc aggtatggct ggagtcccag cgtcgcatc aaaaattgta   1080 acagctctgt cagaaaaagg aattcgtatt ttacaatctg ctgacagcca cacgaccatc   1140
tgggttttag ttaaacaaga ggatttagta aatgcagtca aagcattgca tgacgcattc   1200
cagcttgaga aagaaacgct ggagtttgaa cggatagaat ga                      1242
```

<210> SEQ ID NO 2
<211> LENGTH: 413
<212> TYPE: PRT
<213> ORGANISM: Bacillus methanolicus

<400> SEQUENCE: 2

```
Met Lys Ile Ile Val Gln Lys Phe Gly Gly Thr Ser Val Arg Asp Asp
1               5                   10                  15

Ile Ser Arg Ser Asn Ala Lys Arg His Ile Glu Lys Ala Leu Ala Glu
            20                  25                  30

Gly Tyr Lys Val Val Val Val Ser Ala Met Gly Arg Ser Gly Glu
        35                  40                  45

Pro Tyr Ala Thr Asp Thr Leu Leu Ser Leu Ile Gly Gly Asn Ala Thr
    50                  55                  60

Lys Val Ser Lys Arg Glu Gln Asp Leu Leu Leu Ser Cys Gly Glu Ile
65                  70                  75                  80

Ile Ser Ser Ile Val Phe Thr Asn Met Leu Ile Glu His Gly Ile Arg
                85                  90                  95

Ala Val Ala Leu Thr Gly Ala Gln Ala Gly Phe Arg Thr Asn Asn Asp
            100                 105                 110

His Thr Asn Ala Lys Ile Ile Glu Met Lys Cys Asp Arg Leu Leu Arg
        115                 120                 125

Glu Leu Glu Gln Asn Glu Val Val Val Ala Gly Phe Gln Gly Ala
    130                 135                 140

Ala Lys Asn Gly Asp Ile Thr Thr Ile Gly Arg Gly Gly Ser Asp Thr
145                 150                 155                 160

Ser Ala Ala Ala Leu Gly Ala Ala Leu Asn Ala Glu Trp Ile Asp Ile
                165                 170                 175

Phe Thr Asp Val Glu Gly Ile Met Thr Ala Asp Pro Arg Ile Val Glu
            180                 185                 190

Asn Ala Arg Pro Leu Ser Val Thr Tyr Thr Glu Val Cys Asn Met
        195                 200                 205

Ala Tyr Gln Gly Ala Lys Val Ile His Pro Arg Ala Val Glu Ile Ala
    210                 215                 220

Met Gln Ala Lys Ile Pro Ile Arg Ile Arg Ser Thr Tyr Ser Asp Ser
225                 230                 235                 240

Pro Gly Thr Leu Val Thr Ser Leu Ser Lys Asn Ser Arg Gly Ser Asp
                245                 250                 255

Ile Arg Glu Arg Pro Val Thr Gly Ile Ala His Val Pro Asn Val Thr
            260                 265                 270

Gln Ile Lys Val Phe Ala Lys Lys Asp Gln Tyr Asn Leu Gln Ala Glu
        275                 280                 285

Val Phe Lys Ala Met Ala Asn Glu Lys Ile Ser Val Asp Leu Ile Asn
    290                 295                 300
```

Ile Ser Pro Asn Gly Val Val Tyr Thr Val Met Asn Glu Met Ala Asp
305                 310                 315                 320

Gln Ala Ile Arg Ile Leu Thr Asp Met Gly His Glu Pro Val Val Glu
            325                 330                 335

Arg Asp Cys Ala Lys Val Ser Val Val Gly Ala Gly Met Ala Gly Val
            340                 345                 350

Pro Gly Val Ala Ser Lys Ile Val Thr Ala Leu Ser Glu Lys Gly Ile
            355                 360                 365

Arg Ile Leu Gln Ser Ala Asp Ser His Thr Thr Ile Trp Val Leu Val
    370                 375                 380

Lys Gln Glu Asp Leu Val Asn Ala Val Lys Ala Leu His Asp Ala Phe
385                 390                 395                 400

Gln Leu Glu Lys Glu Thr Leu Glu Phe Glu Arg Ile Glu
            405                 410

<210> SEQ ID NO 3
<211> LENGTH: 1368
<212> TYPE: DNA
<213> ORGANISM: Bacillus methanolicus

<400> SEQUENCE: 3
atgaaagtag cgaagtttgg aggttcttca ttagcatcag agaacaatt tgaaaaggta      60 tttaacattg ttatgtctga tccaaagaga aaaattgttg tagtttcggc accaggcaag    120
cgttttgcga gtgatataaa ggtaaccgat ttactcattg aatgcgccga aaatgccta    180 aaaaacgaag cggctgatga tttagtagaa gccgtcatcg aaagatatgc aagtattgca    240
agggaactgg ggctttcaag cagagtttca aatatgattc gaacgatct tcttacagtg    300 ttaagcggag ataaaagcaa tcctgaacga tttatcgatg ctgttaaagc aaccggcgag    360
gacaataatg caaaacttat ggccgcgtac ttccagcata aggagtaga ggctcgctat    420 gtaaatccga agatgcggg cctgattgta agcgatgagc ctggaaatgc acaagtgctt    480
cctgaatctt atgaacggct ttttgagctt cggaatttgc aggaattat tattttccct    540 ggattttttcg ctttacaaa aaagggagaa gtggtaactt tttcacgaag cggatctgac    600
ataaccggtt ccattttagc gaatgggacg aaagctgagc tttatgaaaa ttttacagac    660
gttgatgcag tttattcagt caatccgaat atcgtggaaa aacctaagga gattcgtgaa    720
ttgacataca gagaaatgcg ggaactctcc tatgctggat tcactgtgct tcatgatgaa    780
gctcttattc ctgctttccg cgccggtatt cctgttaata ttaaaaacac caataatcca    840
tcggctcctg aacgaagat cgttcatgaa cggacaactt cgaatggccc tgtgatcgga    900
attgcaagtg ataaaggatt ctgcagcatt tatgtcagca atatatttaat gaaccgagaa    960 attggattcg gacgaaaaat tttgcagatt ttagaagagt acggattgtc gtatgaacat   1020
attccatccg gaattgatga catctcgatt attctaagaa aaaatcagtt gaatccagcg   1080
ttggaagaag agattgttac acgcattaaa acggagcttg aggctgatga agtgaaaatt   1140
gaacgtaatc ttgctcttat tatgatcgtg ggtgaaggga tgcgccaaaa tgtggggaca   1200
atggctagag cttcaaaggc gctggccgat gcaggcgtca atattgaaat gatcaaccag   1260
ggatcctcag aagtgagcat gatgttcggt gtgaaagctg aagatgaaca acgtgcggtg   1320
atagcccttt acaaagagtt ttttgctcca gttcctgtaa atgttag              1368

<210> SEQ ID NO 4
<211> LENGTH: 455
<212> TYPE: PRT

<213> ORGANISM: Bacillus methanolicus

<400> SEQUENCE: 4

```
Met Lys Val Ala Lys Phe Gly Gly Ser Ser Leu Ala Ser Gly Glu Gln
1               5                   10                  15

Phe Glu Lys Val Phe Asn Ile Val Met Ser Asp Pro Lys Arg Lys Ile
            20                  25                  30

Val Val Val Ser Ala Pro Gly Lys Arg Phe Ala Ser Asp Ile Lys Val
        35                  40                  45

Thr Asp Leu Leu Ile Glu Cys Ala Glu Lys Cys Leu Lys Asn Glu Ala
    50                  55                  60

Ala Asp Asp Leu Val Glu Ala Val Ile Glu Arg Tyr Ala Ser Ile Ala
65                  70                  75                  80

Arg Glu Leu Gly Leu Ser Ser Arg Val Ser Asn Met Ile Arg Asn Asp
                85                  90                  95

Leu Leu Thr Val Leu Ser Gly Asp Lys Ser Asn Pro Glu Arg Phe Ile
            100                 105                 110

Asp Ala Val Lys Ala Thr Gly Glu Asp Asn Asn Ala Lys Leu Met Ala
        115                 120                 125

Ala Tyr Phe Gln His Lys Gly Val Glu Ala Arg Tyr Val Asn Pro Lys
    130                 135                 140

Asp Ala Gly Leu Ile Val Ser Asp Glu Pro Gly Asn Ala Gln Val Leu
145                 150                 155                 160

Pro Glu Ser Tyr Glu Arg Leu Phe Glu Leu Arg Asn Leu Pro Gly Ile
                165                 170                 175

Ile Ile Phe Pro Gly Phe Phe Gly Phe Thr Lys Lys Gly Glu Val Val
            180                 185                 190

Thr Phe Ser Arg Ser Gly Ser Asp Ile Thr Gly Ser Ile Leu Ala Asn
        195                 200                 205

Gly Thr Lys Ala Glu Leu Tyr Glu Asn Phe Thr Asp Val Asp Ala Val
    210                 215                 220

Tyr Ser Val Asn Pro Asn Ile Val Glu Lys Pro Lys Glu Ile Arg Glu
225                 230                 235                 240

Leu Thr Tyr Arg Glu Met Arg Glu Leu Ser Tyr Ala Gly Phe Thr Val
                245                 250                 255

Leu His Asp Glu Ala Leu Ile Pro Ala Phe Arg Ala Gly Ile Pro Val
            260                 265                 270

Asn Ile Lys Asn Thr Asn Asn Pro Ser Ala Pro Gly Thr Lys Ile Val
        275                 280                 285

His Glu Arg Thr Thr Ser Asn Gly Pro Val Ile Gly Ile Ala Ser Asp
    290                 295                 300

Lys Gly Phe Cys Ser Ile Tyr Val Ser Lys Tyr Leu Met Asn Arg Glu
305                 310                 315                 320

Ile Gly Phe Gly Arg Lys Ile Leu Gln Ile Leu Glu Glu Tyr Gly Leu
                325                 330                 335

Ser Tyr Glu His Ile Pro Ser Gly Ile Asp Asp Ile Ser Ile Ile Leu
            340                 345                 350

Arg Lys Asn Gln Leu Asn Pro Ala Leu Glu Glu Glu Ile Val Thr Arg
        355                 360                 365

Ile Lys Thr Glu Leu Glu Ala Asp Glu Val Lys Ile Glu Arg Asn Leu
    370                 375                 380

Ala Leu Ile Met Ile Val Gly Glu Gly Met Arg Gln Asn Val Gly Thr
385                 390                 395                 400
```

Met Ala Arg Ala Ser Lys Ala Leu Ala Asp Ala Gly Val Asn Ile Glu
            405                 410                 415

Met Ile Asn Gln Gly Ser Ser Glu Val Ser Met Met Phe Gly Val Lys
        420                 425                 430

Ala Glu Asp Glu Gln Arg Ala Val Ile Ala Leu Tyr Lys Glu Phe Phe
        435                 440                 445

Ala Pro Val Pro Val Asn Val
        450                 455

<210> SEQ ID NO 5
<211> LENGTH: 1365
<212> TYPE: DNA
<213> ORGANISM: Bacillus subtilis

<400> SEQUENCE: 5
ttaagagatc agcacgcccg cgaaaaattc ctggtataac gcttgaacgg cttttctttc      60
ttcggcttct tttacgccaa acatcatgct cacttcagaa gacccctgat tgatcatttc     120
gatattcacc tgtgcctctg ataatgcttt ggcggctctt gccgttgtac cgacattgtg     180
gcgcatcgct tccccctacaa ccataatcag ggcgagatga tgctcgacga tgacttcatc     240
ggcatgcaaa tcctcttcga tccgtttgat gacgctgcgt tcagtggcgg catccatttg     300
cccctgccgt aaaatgattg tcatgtcatc gattcccgat ggaacatgct catacgtcaa     360
accatgctcc tccaggattt gaagggctct gcggccaaaa ccgatttctc tgttcatgag     420
atacttgctg atataaatgc tgcaaaaacc ggtgtcgctg caatgccga cgacaggccc     480 gtttgtgtta tcccgcttgc tgacgacgcg ggtgccttcg gctgagggt tgttcgtatt     540 tttgatctga acaggaatcc ccgctctgaa tgccggaatg agcgcttcat catgaaacac     600
tgaaaaaccc gcgtaggaca gctcccgcat ctctctatat gtcagctcgc tgatttcctt     660
tggattctca acgaaggacg gattgacaga atacacagcg tctacgtctg taaagttttc     720
gtacaaatcg gcttgtagtc cgttggcaag aatcgaaccg gtaatatcag aaccgctccg     780
tgagaatgtg atcacatcgc catccttgct gaatcgaaaa aaaccgggaa aaatgatgag     840
tccgtcacgt tcccgaagac gatagaggtt ttgataggat tcaggaagaa cttgcgcgtt     900
gccgggttca tttgtcacaa agaggccggc atccttcggg tttacatatt ccgctttgac     960
gcctttataa cggaagtaag cggcgatcag tttggcattg ttatcctctc cgctggcctt    1020
gactgcgtca aggtattgtt cgggattgct tttgtctcct tctaaaagcg taaacagatc    1080
atctctgatt ttttcgataa tgctttgccc cagctgaagc tcattggcga tgagagcgta    1140
ccgttccaca acagcttccg ccagttcagg tgcgctgcct gttgccaaat attgttctgc    1200
acatgcgatt aagagatcag tcactttcgt atcctcggca tagtgttttc ccggagctga    1260
aacgactaca gctttccgtg ccggatctga ggtaacgatg tgaaacacct tgtcaagctg    1320
ggcgcctgaa gcaagtgagc tgcctccgaa tttaacgacc ttcat                    1365

<210> SEQ ID NO 6
<211> LENGTH: 1362
<212> TYPE: DNA
<213> ORGANISM: Bacillus licheniformis

<400> SEQUENCE: 6
ttaaacgaga acttttgcga aaaactcctg gtataatgcg cggaccgctt gttttcctg      60 agcttccctta acgccgaaca tcatgctgac ttccgaggag ccctggttga tcatttcgat    120
gttgacgccg gcttcagaca atgctttga cgctcttgcc gtcgttccga cgttatggcg     180

-continued

```
catggcttcg ccgacgacca tgatcagggc aatattgtgt tcaatcgcta cttcatcagc        240
atccaactct tccttgatcc gtttgatcat ccgttttct gctgcttgat ccatttgatt        300
ctgccttaaa atgatcgtaa tatcgtcaat gccggacgga atgtgttcat atgtcagccc        360
ttcatcttca aggatttgca ggacgcggcg gccgaagccg atttctcggt tcatcaaata        420
tttgctgatg taaatgctgc aaaatccgct gtcgccggcg atcccgacga caggtccgtt        480
cgtgttgtcg cgtgtggcga caactcttgt cccttctgcg tccgggttgt ttgtatttt         540 gatctgaacc ggtatgcgcg cccggaaagc agggatcaat gcttcatcat gaaagacgga        600
aaagccggca tacgacagct ctctcatttc ccggtatgtc agctcgcgga tttctttcgg        660
gttggatacg atcgccgggt tgacagaata acggcgtca acgtcagtga agttttcata         720
caactcggct ttcaatccat tcgctaaaat ggagcccgta atgtcagagc cgctgcgcga        780
aaacgtcatc acttctcctt cctggctgaa tccgaagaag ccgggaaaga taatgatgcc        840
cttttgctgt ctgagctgaa acagattgtc gtaggactcg ggcagcactt gtgcgttgcc        900
gggttcgctc gtcacgaaca gcccggcgtc ttttggactg acataatgtg cttcaactcc        960
acggtgcctg aagtaggccg ctaccagttt ggcattgtta tcttcgccgc tagctttgat       1020
cgcatcaata aaccgttccg gatttgtttt atcaccttcg agcagctgaa gcaggtctgc       1080
ccggatccgg ttgatcacgt catcggcaag cccgagctct agcgcgatat cggcataccg       1140
tccgacaatc gcctcaacca ggccggtcgc ttctttcgat aataggtact gttgggcgca       1200
ttcgattaac aggtcagtta ctttcgtatc ctcgggatgc cgttttccgg gtgccgatac       1260
gacgacggcc ctcctttccg gatcggaagt gacgatttga atactttct ctagctgggc        1320 tcctgatgcg agcgagctgc ctccaaattt aacgactttc at                         1362
```

<210> SEQ ID NO 7
<211> LENGTH: 1371
<212> TYPE: DNA
<213> ORGANISM: Bacillus halodurans

<400> SEQUENCE: 7

```
atgaaagtaa cgaagtttgg tggaacatcc gttgcgagtg cagagcaaat tcgcaaggtg         60
gctacgattg tagcagatga tgtggagcgt aaaattgtcg tcgtttcagc tcctgggaag        120
cggcattcaa gcgatacaaa ggtgacggat ttgttaattc gtttaggaga aacgtactta        180
gaaaagggat atgcgaatga ggagctagag gcggttttac gacggtatga agaaattgct        240
aaagggttgg agctcggcca agagatcatt gatcaaattg cgaacgattt acacacaagg        300
ctaaccttta accaaagcaa ccccggtgca tttatggatc aactcaaggc aagcggggag        360
gacaacaacg cgaagttaat tgctgcctat ttgcaaacca aggaatgaa tgcagtctat         420 gtaagcccaa aggaggccgg cctgttggtc agtgatgaac ctggaaacgc caagtgtta         480 cctgaggcgt atgaccattt aaaaaagctt cgtgaacgtg acgaaatgat cgtattccca        540 ggttttttg gtttttctcc agacggagct ctcgtcacat ttccgcgagg aggctcggac        600
attactggag cgattttggc cgctgggggtg aaagcggaac tgtatgagaa ttttacagac       660
gtggattccg tgtttgctgc gaacccaaat gtcgttgaaa gtccggcgca aattcggcgc        720
atgacttata gagaaatgcg ggagcttttcc tatgcgggct tttccgtctt tcatgatgaa       780
gcgttaattc cagcatttcg gcaaaagatt ccgttgtgt gaaaaacac gaacaatcct         840 agctcaccag gaacaatgat tctagcagag cgagagtact tttaaatcc tgtcatcggg        900
```

```
attgcggcag ataaagggtt tgcgactatt tatgttcgca aatatttaat gaaccgtgaa      960 ataggggttcg ggcgtcggct gttgcaaatt attgaagatg aaggcctttc atatgagcat     1020
atcccgtcag gaattgatga tgcctcggtc attcttcggc aggagcaact gacggatgaa     1080
atcgagcatc ggatattagc acgaataaaa gaggagcttt gtgtcgacga tgtgttttgtt    1140 gaaaaggatt ttgctatggt gatgatcgtt ggtgaaggaa tgcataacac tgtcggcatt     1200
tcagcacgag ccacggctgc gcttgctaga gctcatgtca acattgaaat gattaaccaa     1260
ggatcgtctg aggttagttt agtgcttggc atacacgaga aagacgccga tgcggccgtc     1320
cgtgaattgt atgaagaatt tttcggtggt gccgaggaaa cggttcaata a              1371
```

<210> SEQ ID NO 8
<211> LENGTH: 1365
<212> TYPE: DNA
<213> ORGANISM: Bacillus amyloliquefaciens

<400> SEQUENCE: 8

```
ctatgagagt aagactccgg cgaaaaattc gtcatacagt gcccgcaccg cgtgttttc       60 ctgttcttct ttcactccga acatcatgct gacttccgat gacccttgat tgatcatctc     120
gatgttgacg ccggcttccg acagtgcttt ggatgccctg gcggttgtgc cgacattatg     180
gcgcatcgct tccccgacga ccataatcag cgccagattg tgcctgactg tgacttcatc     240
tgcttgaagt tcctgcttca gacgggtgac gagcctgtgt tccagttctg agtccatctg     300
attgtgccga aggatgatcg tgatgtcgtc aatgccggat ggaacgtgtt catacgtcaa     360
tccttcttcc tccaaaatgt gaagggcttt gcggccgaaa ccgatttccc ggttcattaa     420
atatttgctt atgtaaatgc tgcaaaagcc cgtgtcgctt gcgatgccga tgactggccc     480
gttcgtattg tcacggctgc tgacgacgcg tgttcctttc gcatccggat tattcgtatt     540
cttaatttga acggggatgc cggcccgaaa tgcgggaatc agcgcttcat catgaaaaac     600
ggaaaatccg gcataggaga gctcacgcat ttcccgatac gtcagttcgt taatttctt     660 cggatgccgc acgattgacg ggttgacgga atagacggca tccacatcag taaagttttc     720
gtacaggtcg gcttttaagc cgctggcgag aatggagccg gtaatatcag aaccgctccg     780
ggaaaacgtc acaatctcat gctccttcgt gtaaccgaaa aatcccggaa aaatgatcaa     840
tccttcacgg tttctcagac ggtacaaatg accataagac tcaggagca cctgcgcgct     900 tccgggttca tccgtcacaa acagccccgc ttctttcgga cttacgtatt ccgctttcac     960
gccctgccgt cggaagtagg ctgcgatcag cttcgcgttg ttgtcctcgc cgctcgcctt    1020
caccgcatcc atatattgtt cgggattggt tttacagctg tttaaaagag cgaataggtc    1080
actgcggatt ctttctataa tagagaaatc caggttcagc tcacgcgcga tggcggcgta    1140
ccgttcaatg accgtttcgg caagctcggg cgctacacct ttttgcaaat aatgctccgc    1200
acagcggatt aacagatccg tcacctttgt atcgtccgag aagcgttttc ccggtgccga    1260
tacgacgacg gctttccgcg cgggatcagc cgtcacgatt tgaaacactt tctcaagctg    1320
tgctcctgac gcaagagagc tgcctccgaa ttttacaact ttcat                     1365
```

<210> SEQ ID NO 9
<211> LENGTH: 1394
<212> TYPE: DNA
<213> ORGANISM: Listeria innocua

<400> SEQUENCE: 9

```
atgaaagtaa ttaaatttgg cggaagctct ttagcatcag ggattcaatt aaataaggtt       60
```

```
ttccaacttg tagcggagga ttctgaacga aagatcgtcg ttgtttctgc acctggaaag    120
cgtttcaagg acgatacaaa agtgaccgat ttacttattg attgtgcggc aaaagcactt    180
ctaggcgaag atacgagtga actatttgaa gccgtcattg cgagatatgc tggcattgcc    240
cttgatacag gaatggatga cgcgattatc acacaaattc gcgccgactt acaaaagact    300
atttcgtctg ataaaagcga tcctgataaa tttttagatc gaatgaaggc tagtggagaa    360
gacaataatg cgaaattaat cgctgcttat tttaaattca aaggcttaaa cgccaactat    420
gttaatccaa aagatgctgg attatttgtg acggatgaac atgctagtgc ccaagttctt    480
cctgagtctt atgaccgttt atttgcgctt cgagagcgag aaggtatcat tgttttttcca   540 ggattttccg ttatacgaa agacggtgaa atcagtacat tttctcgaag tggctctgat     600
attactggag cgattgtcgc aaacgggggct caagctgagt tatacgagaa ctttactgat   660
gttgatgcag tgtatgcggt caatcccgct attgtgaaaa atccgaagaa agttcttgaa   720
ctgacttacc gggaaatgcg cgaactttct tatgcaggct tttctgtttt tcatgatgaa   780
gcactgattc cggcgttcca tgcgggtatt cctgtgcata ttaaaaatac gaacaatcct   840
gattcttgtg gtacacgtgt cgttcatgaa cgcgaaaaca ataatggtcc tgtcgttggt   900
attgctagtg atgatggctt ttgtagcatt tatattagta aatatttgat gaaccgcgaa   960
attggcttcg gacggaaagt gctgcaaatt ctggaagatg ctggattgaa ttatgaacat  1020
atgccgtctg ggattgatga tttaacgatt attattcgtg aaaatcagtt tggtgaggac  1080
acagagcgga cgattatgac gcggttaaaa gaagaattaa atgccgatca agtgattatg  1140
caacatggta tctccctgat tatggtcgtt ggtgaagcta tgcgccataa tgttggaata  1200
acctcgcgtg cttcgaaagc tttatctgac gcgaaagtga atattgaaat gattaatcaa  1260
ggttcttctg aagtaagtat tatgtttggt gtgaaggaag aacaggaaaa tacggccgtt  1320
cgcgcactat acaatgaatt cttttcagaa gtcttagtct aacaagtttt tcatcctgat  1380
tgatgagaaa cttg                                                    1394

<210> SEQ ID NO 10
<211> LENGTH: 20
<212> TYPE: DNA
<213> ORGANISM: Artificial sequence
<220> FEATURE:
<223> OTHER INFORMATION: primer

<400> SEQUENCE: 10
tctaccttcg ttgaggaaga                                                20

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
cactcctgaa cggttaatcc                                                20

<210> SEQ ID NO 12
<211> LENGTH: 20
<212> TYPE: DNA
<213> ORGANISM: Artificial sequence
<220> FEATURE:
<223> OTHER INFORMATION: primer
```

<400> SEQUENCE: 12
tgagcagaca agagcgatta                                              20

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
atagatcgct ccgatatggt                                              20

<210> SEQ ID NO 14
<211> LENGTH: 35
<212> TYPE: DNA
<213> ORGANISM: Artificial sequence
<220> FEATURE:
<223> OTHER INFORMATION: primer

<400> SEQUENCE: 14
cctgtgatcg gaattgcaag tgataaagga ttctg                             35

<210> SEQ ID NO 15
<211> LENGTH: 35
<212> TYPE: DNA
<213> ORGANISM: Artificial sequence
<220> FEATURE:
<223> OTHER INFORMATION: primer

<400> SEQUENCE: 15
atcttcgttc caggagccga tggattattg gtgtt                             35

<210> SEQ ID NO 16
<211> LENGTH: 25
<212> TYPE: DNA
<213> ORGANISM: Artificial sequence
<220> FEATURE:
<223> OTHER INFORMATION: primer

<400> SEQUENCE: 16
tcgacatgtg acaacaaact ttttc                                        25

<210> SEQ ID NO 17
<211> LENGTH: 25
<212> TYPE: DNA
<213> ORGANISM: Artificial sequence
<220> FEATURE:
<223> OTHER INFORMATION: primer

<400> SEQUENCE: 17
acgcatacca ttttgaacga tgacc                                        25

<210> SEQ ID NO 18
<211> LENGTH: 30
<212> TYPE: DNA
<213> ORGANISM: Artificial sequence
<220> FEATURE:
<223> OTHER INFORMATION: primer

<400> SEQUENCE: 18
gccggatcct gcagttcatt aaagagcagc                                   30

<210> SEQ ID NO 19
<211> LENGTH: 27

```
<212> TYPE: DNA
<213> ORGANISM: Artificial sequence
<220> FEATURE:
<223> OTHER INFORMATION: primer

<400> SEQUENCE: 19
cgcgacatgt actacctcct atttatg                                    27

<210> SEQ ID NO 20
<211> LENGTH: 26
<212> TYPE: DNA
<213> ORGANISM: Artificial sequence
<220> FEATURE:
<223> OTHER INFORMATION: primer

<400> SEQUENCE: 20
cgcggcatgc gtttcaatga agatcc                                     26

<210> SEQ ID NO 21
<211> LENGTH: 26
<212> TYPE: DNA
<213> ORGANISM: Artificial sequence
<220> FEATURE:
<223> OTHER INFORMATION: primer

<400> SEQUENCE: 21
ttaagcatgc aaaaggccag gaaccg                                     26

<210> SEQ ID NO 22
<211> LENGTH: 26
<212> TYPE: DNA
<213> ORGANISM: Artificial sequence
<220> FEATURE:
<223> OTHER INFORMATION: primer

<400> SEQUENCE: 22
ttttggtacc cgccataggt ctagag                                     26

<210> SEQ ID NO 23
<211> LENGTH: 27
<212> TYPE: DNA
<213> ORGANISM: Artificial sequence
<220> FEATURE:
<223> OTHER INFORMATION: primer

<400> SEQUENCE: 23
gggcggtacc ttattcttta gtctatc                                    27

<210> SEQ ID NO 24
<211> LENGTH: 24
<212> TYPE: DNA
<213> ORGANISM: Artificial sequence
<220> FEATURE:
<223> OTHER INFORMATION: primer

<400> SEQUENCE: 24
ccgaacatgt gggattaatt gtcc                                       24

<210> SEQ ID NO 25
<211> LENGTH: 26
<212> TYPE: DNA
<213> ORGANISM: Artificial sequence
<220> FEATURE:
<223> OTHER INFORMATION: primer

<400> SEQUENCE: 25
```
ttccggtacc cagcaaattg aacagc                                    26

<210> SEQ ID NO 26
<211> LENGTH: 34
<212> TYPE: DNA
<213> ORGANISM: Artificial sequence
<220> FEATURE:
<223> OTHER INFORMATION: primer

<400> SEQUENCE: 26
gcgcacatgt gaaaattatc gttcaaaaat tcgg                            34

<210> SEQ ID NO 27
<211> LENGTH: 28
<212> TYPE: DNA
<213> ORGANISM: Artificial sequence
<220> FEATURE:
<223> OTHER INFORMATION: primer

<400> SEQUENCE: 27
gctaggtacc gctcctcctc attctatc                                  28

<210> SEQ ID NO 28
<211> LENGTH: 37
<212> TYPE: DNA
<213> ORGANISM: Artificial sequence
<220> FEATURE:
<223> OTHER INFORMATION: primer

<400> SEQUENCE: 28
gcgcacatgt gaaagtagcg aagtttggag gttcttc                        37

<210> SEQ ID NO 29
<211> LENGTH: 31
<212> TYPE: DNA
<213> ORGANISM: Artificial sequence
<220> FEATURE:
<223> OTHER INFORMATION: primer

<400> SEQUENCE: 29
gctaggtacc agtgtttcac acccaaattc g                              31

<210> SEQ ID NO 30
<211> LENGTH: 30
<212> TYPE: DNA
<213> ORGANISM: Artificial sequence
<220> FEATURE:
<223> OTHER INFORMATION: primer

<400> SEQUENCE: 30
gcgcacatgt gggtcaagaa aatggtcttc                                30

<210> SEQ ID NO 31
<211> LENGTH: 27
<212> TYPE: DNA
<213> ORGANISM: Artificial sequence
<220> FEATURE:
<223> OTHER INFORMATION: primer

<400> SEQUENCE: 31
atggtacctg ccccgaatt tttgaac                                    27

<210> SEQ ID NO 32
<211> LENGTH: 31
<212> TYPE: DNA
<213> ORGANISM: Artificial sequence

```
<220> FEATURE:
<223> OTHER INFORMATION: primer

<400> SEQUENCE: 32
gcgcacatgt ggtttcattt ggtcgaatat c                              31

<210> SEQ ID NO 33
<211> LENGTH: 29
<212> TYPE: DNA
<213> ORGANISM: Artificial sequence
<220> FEATURE:
<223> OTHER INFORMATION: primer

<400> SEQUENCE: 33
atggtaccgg cagtaaaaac tccattgat                                 29

<210> SEQ ID NO 34
<211> LENGTH: 29
<212> TYPE: DNA
<213> ORGANISM: Artificial sequence
<220> FEATURE:
<223> OTHER INFORMATION: primer

<400> SEQUENCE: 34
gcgcacatgt gtattttcat ggcacaaca                                 29

<210> SEQ ID NO 35
<211> LENGTH: 28
<212> TYPE: DNA
<213> ORGANISM: Artificial sequence
<220> FEATURE:
<223> OTHER INFORMATION: primer

<400> SEQUENCE: 35
atggtaccgc agcttagtat cttactct                                  28
```

METHOD OF L-LYSINE PRODUCTION

The present application is a 371 of PCT/GB2009/001265 filed May 15, 2009.

The present invention concerns methods of microbial production of L-lysine from methanol and other substrates, and particularly improving the production of L-lysine from such substrates. In particular, the methods of the invention involve over-expression of an aspartokinase III (AKIII) enzyme in the producing microorganism, which preferably may be *Bacillus methanolicus*. This may be achieved by modifying the microorganism to express an AKIII-encoding gene, for example under the control of a promoter which may be non-native (or heterologous) to that gene. Thus, notwithstanding that the microorganism may naturally express an (endogenous) AKIII, a further copy (or more) of that AKIII, or of another AKIII, may be expressed, or the microorganism may otherwise be modified to over-express AKIII e.g. by mutagenesis, followed by appropriate selection.

Amino acids are among the major products in biotechnology in both volume and value, and the global market is growing. They are used as food and feed supplements, pharmaceuticals, cosmetics, polymer materials and agricultural chemicals (Ikeda (2003) Amino Acid Production Processes In: Faurie et al., (Eds) Advances in Biochemical Engineering Biotechnology: Volume 79, Microbial Production of L-amino acids. Springer: Berlin, Heidelberg, N.Y.; Marx et al., (2006) Protein line and amino acid-based product family trees. In: Kamm et al., Biorefineries—industrial processes and products. Status quo and future directions. Wiley-VCH: Weinheim pp. 201-216). Microbial fermentation is the dominant method used for industrial production, and today the most important microorganisms used are *Corynebacteria*, utilising sugars. The most important industrial amino acid producer today is the bacterium. *Corynebacterium glutamicum*, which produces about 2 million tons of amino acids per year, above 1 and 0.6 million tons of L-glutamate and L-lysine, respectively (Eggeling et al., (2005), Handbook of *Corynebacterium glutamicum*. Taylor and Francis: Boca Raton). The substrate for *C. glutamicum* fermentation is generally sugar from agricultural crops.

There is a growing global demand for amino acids, and the possibilities to utilise alternative substrates as feedstock in fermentation is therefore also of considerable interest. One-carbon ($C_1$) compounds occur abundantly throughout nature, and methane and methanol are two of the most important $C_1$ compounds from a biotechnological and a bulk chemical point of view (Linton et al., (1987) Antonie Van Leeuwenhoek, 53: 55-63). Compared to molasses, for example, methanol is a pure raw material that can be completely utilized during bacterial fermentations.

Methylotrophs comprise the large number of both aerobic and anaerobic microorganisms that can grow on reduced compounds lacking C—C bonds, such as methane and methanol (Anthony (1982) The biochemistry of methylotrophs. Academic Press: New York; Large et al., (1988) Methylotrophy and biotechnology. Wiley: New York). Obligate methylotrophs can exclusively utilize $C_1$ compounds as a sole carbon and energy source, while facultative methylotrophs can utilize both $C_1$ and multicarbon compounds. Genetic tools for many methylotrophs have been established, and engineering of methylotrophs leading to overproduction of different amino acids are reported including L-serine (Izumi et al., (1993) Appl. Microbiol. Biotechnol., 39: 427-432; Hagishita et al., (1996) Biosci. Biotechnol. Biochem., 60: 1604-1610), L-threonine (Motoyama et al., (1994) Appl. Microbiol. Biotechnol., 42: 67-72), L-glutamate (Motoyama et al., (1993) Biotechnol. Biochem., 57: 82-87), and L-lysine (Motayama et al., (2001) Appl. Environ. Microbiol., 67: 3064-3070). For example, in the Gram-negative obligate methylotroph *Methylophilus methylotrophus*, the expression of a mutant gene encoding dihydrodipicolinate synthase deregulated in L-lysine inhibition caused increased L-lysine synthesis to about 1 g/l at 37° C. (Tsujimoto et al., (2006) J. Biotechnol., 124: 327-337). By co-expressing a mutant gene encoding an L-lysine transporter they obtained a recombinant strain, strain AS1 (pSEA10), secreting 11.3 g/l of L-lysine from methanol (Gunji et al., (2006) J. Biotechnol., 127(1): 1-13). A recombinant mutant, AL119 (pDYOM4-2), of the Gram-negative obligate methyotroph *Methylobacillus glycogenes*, overexpressing a dihydrodipicolinate synthase partly deregulated in L-lysine inhibition was reported to produce about 8 g/l of L-lysine and 37 g/l of 1-glutamate from methanol at 37° C. (Motayama et al., (2001), supra). Notwithstanding the foregoing, no commercial methanol-based industrial production process for any amino acid is presently thought to exist.

The methylotrophic thermotolerant bacterium *B. methanolicus* may represent a promising candidate for the bioconversion or methanol into amino acids (Brautaset et al., (2007) Appl. Microbiol. Biotechnol., 74: 22-34). Favourable properties of *B. methanolicus* include lack of sporulation at high temperatures, utilisation of methanol as energy and carbon source, high methanol conversion rate, and an optimal growth temperature of 50° C. *B. methanolicus* mutants produced by random chemical mutagenesis have been reported to produce up to 37 g/l of L-lysine (Schendel et al., (1990) Appl. Environ. Microbiol., 56: 963-970). Whilst methanol may represent an attractive substrate, *B. methanolicus* may utilise other substrates including multi-carbon substrates such as sugars (e.g. mannitol). Accordingly, *B. methanolicus* is of interest as a "host" or organism for production of L-lysine, irrespective of substrate (i.e. not necessarily using methanol as substrate).

L-lysine is synthesised from L-aspartate as part of the aspartate pathway which also includes the biosynthetic pathways for L-methionine and L-threonine (FIG. 1). The first step of the aspartate pathway is controlled by aspartokinase ("AK"; ATP:4-L-aspartate-4-phosphotransferase). This enzyme is generally heavily feedback-regulated by products of the aspartate pathway, both in respect to enzyme activity (inhibition) and enzyme synthesis (repression). Deregulation of AK (i.e. removal of inhibition of enzyme activity) has been reported to be the most important step in the development of commercial L-lysine producing strains (Pfefferle et al., (2003) Biotechnological manufacture of lysine. In: Faurie et al., (Eds) Advances in Biochemical Engineering Biotechnology: Volume 79, Microbial Production of L-amino acids. Springer: Berlin, Heidelberg, N.Y., pp. 59-112), and it has been stated that metabolic engineering further to improve L-lysine production of *B. methanolicus* should focus on deregulating key enzymes in the L-lysine biosynthetic pathway (Brautaset et al., (2007) supra). Indeed, a number of favourable mutations causing deregulation of AK feedback inhibition (i.e. resistance to allosteric inhibition) in the commercial L-lysine producer *C. glutamicum* have been reported (Ohnishi et al., (2002) Appl. Microbiol. Biotechnol., 58: 217-223; Eggeling et al., (2005) supra; Jakobsen et al., (2006) J. Bacteriol., 188(8): 3063-3072); Cremer et al., (1991) Appl. Environ. Microbiol., 57(6): 1746-1752; Jetten et al., (1995) Appl. Microbiol. Biotechnol., 43(1): 76-82).

While *C. glutamicum* has a single AK enzyme, the well-studied *B. subtilis* is known to possess three AK isoenzymes, AKI, AKII and AKIII. Generally, little attention has been given to studies of the effects of manipulations involving AK on L-lysine production in *B. subtilis*. The L-lysine analogue S-(2-aminoethyl)cysteine (AEC) has been used extensively to generate microbial L-lysine overproducers, by classical mutagenesis followed by selection. Although decreased feedback inhibition of AKI and AKII was demonstrated in *B. subtilis*, improved L-lysine production was not reported (Zhang et al., (1990) J. Bacteriol., 172(8): 4690-4693). Mutations in some AEC-resistant *B. subtilis* mutants were mapped to the 5' untranslated RNA leader of lysC (encoding AKII), and correlated with decreased repression and an increase in L-lysine production. However, significant L-lysine production (exceeding 1 g/l) by such mutants has not been reported (Vold et al., (1975) J. Bacteriol., 121(3): 970-974). The inventors are not aware of any reports describing mutations in AKIII in *B. subtilis* which lead to increased L-lysine production.

Until now, in *B. methanolicus* only lysC encoding AKII has been known (Schendel et al., (1992) Appl. Environ. Microbiol., 58(9): 2806-2814). The present invention has been facilitated by the cloning and sequencing by the present inventors of the genes encoding AKI (dapG) and AKIII (yclM) of *B. methanolicus*, as discussed in more detail below.

As discussed above, efforts to increase the microbial production of L-lysine have mainly concentrated on deregulation of AK by using AK mutants resistant to allosteric inhibition by products of the pathway. There have been no reports of the successful use of wild-type AK in significantly increasing L-lysine production. When the *C. glutamicum* gene encoding wild-type AK was expressed from a plasmid in *C. glutamicum*, no L-lysine was produced. However, L-lysine was produced in a *C. glutamicum* transformed with a plasmid expressing a mutant, feedback-resistant AK, suggesting that in the former case the feedback-sensitivity of the wild-type AK was responsible for the lack of L-lysine production (Cremer et al., (1991), supra). In another study, *C. glutamicum* carrying plasmids from which the wild-type AK-encoding gene is expressed from a heterologous promoter was unable to grow on defined medium (Koffas et al., (2003) Metab. Eng., 5(1): 32-41). In experiments involving the overexpression of the wild-type *C. glutamicum* (but referred to as *B. flavum*) AK-encoding gene from its native promoter, while a 33% increase in L-lysine production was observed in an AEC-resistant, L-lysine-overproducing *C. glutamicum* strain, no increase was reported when a wild-type strain was used (Lu et al., (1994) Biotechnol. Lett., 16(5): 449-454). An increase of 20% in L-lysine synthesis flux was observed when a gene encoding a feedback-resistant AK was overexpressed in a *C. glutamicum* strain natively expressing a wild-type feedback-sensitive AK (Hua et al., (2000) J. Biosc. Bioeng., 90(2): 184-192). It was previously, therefore, accordingly believed that, consistent with the above-stated view in the art that deregulation of AK is the most important step in developing L-lysine overexpressing strains, overexpression of wild-type AK would not be sufficient to achieve significant increases in L-lysine production due to, for example, the feedback inhibitory effects of pathway products on AK enzyme activity. As mentioned above, despite resulting in decreased repression, high L-lysine production was not demonstrated for *B. subtilis* AEC-resistant mutants in which the mutations mapped to the 5' UTR of lysC (encoding AKII) (Vold et al., (1975) supra; Mattioli et al., (1979) J. Gen. Microbiol., 114: 223-225).

Surprisingly, the present inventors have now found that overexpression of a yclM gene encoding AKIII results in significantly increased production of L-lysine. Significantly, this result may be achieved using a gene encoding a wild-type enzyme, that is an enzyme which is subject to feedback inhibition. By over-expressing yclM by expressing a yclM gene (i.e. an exogenously-introduced yclM gene) using a strong, promoter non-native to the AKIII gene, a 60-fold increase in L-lysine production has been achieved, with no requirement to use a feedback inhibition-resistant mutant of AKIII. Such a significant increase was not observed with AKI (dapG) or AKII (lysC), using which much lower increases in L-lysine production (2-fold and 10-fold, respectively) were observed. The effect is thus particular to the AKIII isoform. The effect of AKIII over-expression is demonstrated particularly in *B. methanolicus* including on both methanol and sugar substrates. It is therefore proposed that over-expression of AKIII, howsoever achieved, represents a mechanism for increasing microbial lysine production.

As discussed further below, the present invention arises in part from the cloning by the inventors of the yclM (encoding AKIII) and dapG (encoding AKI) genes of *B. methanolicus*. The AKIII of *B. methanolicus* may be used to achieve overexpression both in a *B. methanolicus* host organism and in other organisms. A particularly notable increase in L-lysine production was observed when wild-type *B. methanolicus* AKIII was overexpressed from a strong, non-native promoter in wild-type *B. methanolicus*. It is surprising that over-expression of only a single gene (yclM) may achieve this effect; the increase may be observed in a wild-type host containing no other modifications or mutations of relevance to the L-lysine production pathway. This is the first report of the expression of the AKIII isoform in particular to increase L-lysine production and of the successful overexpression of any gene in *B. methanolicus* to increase L-lysine production.

The magnitude of the increase which may be obtained, e.g. up to 60-fold, as observed in a wild-type host, is surprising and could not have been predicted. Before the present invention, increases in L-lysine production of only 33% and 20% (i.e. less than 1.5-fold) were achieved in *C. glutamicum*.

As mentioned above, the over-expression of an AKIII gene results in an order of magnitude-greater increase in L-lysine production, which could not have been foreseen. The present invention would thus clearly be of great value in helping to meet the increasing need for L-lysine. In particular *B. methanolicus* may beneficially be used as a host for producing L-lysine, using both methanol and other substrates (i.e. other carbon sources such as sugars) as feedstock.

In one aspect, therefore, the present invention provides a method for producing L-lysine in *B. methanolicus*, said method comprising overexpressing an AKIII enzyme in said *B. methanolicus*. The AKIII enzyme may be defined as an enzyme having AK activity which is encoded by a yclM gene.

Alternatively viewed, this aspect of the invention provides a method for increasing the production of L-lysine in *B. methanolicus*, said method comprising overexpressing an AKIII enzyme in said *B. methanolicus*.

The method of this aspect of the invention is thus a method in which *B. methanolicus* is cultured or grown using any desirable carbon source as a substrate, including but not limited to methanol, under conditions in which lysine may be produced. A *B. methanolicus* host cell is used which has been modified to over express AKIII (e.g. engineered or mutated in such a manner that AKIII is overexpressed in the host cell, for example by introducing into a *B. methanolicus* host cell a gene encoding an AKIII enzyme or by randomly mutating a *B. methanolicus* host cell and selecting a mutant which over expresses AKIII, or by site-directed or other mutagenesis to achieve over-expression of the endogenous AKIII). The method of the invention may thus in one embodiment comprise culturing or growing a *B. methanolicus* host, cell which contains an exogenously-introduced AKIII-encoding gene (i.e. a *B. methanolicus* which is transformed with an AKIII-encoding gene), and more specifically a yclM gene.

In another aspect, the present invention provides a *B. methanolicus* organism which overexpresses an AKIII enzyme.

More particularly, this aspect of the invention provides a *B. methanolicus* organism which has been modified to overexpress an AKIII enzyme. In one particular embodiment such modification may comprise introducing into said organism a gene (or more generally put, a nucleic acid molecule) encoding an AKIII enzyme, more specifically a yclM gene.

The AKIII enzyme may be any AKIII enzyme from any source, including both known enzymes reported in the literature or as yet unknown enzymes cloned from a desired source, and reference to AKIII includes any enzyme having the function or activity of *B. methanolicus* AKIII or any enzyme considered to correspond homologously to *B. methanolicus* AKIII on the basis of amino acid sequence identity or similarity, or by virtue of the identity or similarity of the encoding nucleic acid sequence to yclM of *B. methanolicus*. In one aspect the AKIII enzyme is an enzyme having AK activity which is encoded by a yclM gene. Thus, the AKIII of *B. methanolicus* may be used as detailed below, including both the native ("wild-type") AKIII/yclM of *B. methanolicus* as set out in SEQ ID Nos 3 and 4 or AKIII/yclM sequences which are functionally equivalent to SEQ ID No. 3 and/or 4 e.g. sequences which are homologous thereto (e.g. as expressed by % sequence similarity or identity as set out below) and represent, or encode a polypeptide having AKIII activity. This includes "variants" of yclM/AKIII, e.g. which encode or are mutant proteins retaining AKIII activity, e.g. feedback-resistant mutants. It will be apparent that, while aspartokinase activity is a prerequisite of the protein overexpressed according to the invention, advantages in terms of the degree of increase in L-lysine production may be obtainable through the use of non-wild-type AKIII protein sequences which have altered properties but which retain AK activity, e.g. feedback inhibition-resistant AKIII mutants. Thus, while a surprising advantage of the invention is that an unexpected increase in L-lysine production can be obtained by overexpression of a wild-type AKIII sequence, namely an AKIII which has the functional characteristics of a wild-type AKIII and more particularly an AKIII which is sensitive to feed-back inhibition (e.g. by a product of the aspartate pathway e.g. lysine and/or threonine etc), it may be desirable to enhance this effect through the use of particular AKIII "variants", for example a variant which is feedback inhibition-resistant. The AKIII may be obtained or derived from any appropriate organism, more particularly a microbial or bacterial organism and in particular from a *Bacillus*. A representative AKIII which may for example be used according to the invention may be obtained or derived from *B. subtilis*, *B. licheniformis*, *B. halodurans*, *B. amyloliquefaciens* or *Listeria innocua* (see for example the AKIII of *Bacillus subtilis* subsp. *subtilis* str. 168, as described in Kunst et al., 1997, Nature, 390, 249-256 (GenBank accession number: NC_000964) (SEQ ID NO: 5); *Bacillus licheniformis* ATCC 14580 (DSM 13) as described in Rey, et al., 2004, Genome Biol., 5, R77 (GenBank accession number: NC_006270) (SEQ ID NO: 6); *Bacillus halodurans* C-125 as described in Takami et al., 2000, Nucleic Acids Res., 28, 4317-4331 (GenBank accession number: NC 002570) (SEQ ID NO: 7); *Bacillus amyloliquefaciens* FZB42 as described in Chen, et al., 2007, Nat. Biotechnol., 25, 1007-1014 (GenBank accession number: CP000560) (SEQ ID NO: 8); or *Listeria innocua* Clip11262 as described in Glaser et al., 2001, Science 294, 849-852 (GenBank accession number: AL596172) (SEQ ID NO: 9) (SEQ ID NO: 9). It will be noted that the GenBank accession numbers referred to above are for the whole genome and accordingly in terms of reference to AKIII sequences reference is made particularly to the AKIII-encoding parts thereof, namely the AKIII-encoding genes or nucleotide sequences contained within the GenBank deposits.

An AKIII "derived from" such a known AKIII may include for example an enzyme encoded by a variant or fragment (part) of that gene or nucleotide sequence, for example a variant having at least 50, 55, 60, 65, 70, 75, 80, 85, 90, 95% or more sequence identity to the published or a deposited sequence. Alternatively such an AKIII may have an amino acid sequence which has at least 50, 55, 60, 65, 70, 75, 80, 85, 90, 95% or more sequence identity to the published/deposited amino acid sequence, or to the amino acid translation of the published/deposited nucleotide sequence. A "part" of the published/deposited nucleotide or amino acid sequence may include or comprise at least 50, 55, 60, 65, 70, 75, 80, 85, 90, 95% or more contiguous nucleotides or amino acids. More particularly it may be an AKIII which is, or which is derived from, the *B. methanolicus* AKIII, as detailed above or below. Particularly preferably, the AKIII is wild-type or sensitive to feedback inhibition i.e. it is not a deregulated enzyme in terms of enzyme activity. It is also preferred for the AKIII enzyme to be thermostable, e.g. capable of operating at temperatures of up to 40° C., 50° C., 60° C., 70° C. or 80° C.

Whilst *B. methanolicus* is a preferred microorganism for production of lysine according to the invention, the effect of AKIII over-expression in increasing production of lysine is not limited to this organism and extends to any microbial host. In other words any microorganism may be used as the organism for lysine production.

Thus, in an alternative aspect, the present invention provides a method for producing L-lysine in a microorganism, said method comprising over-expressing in said microorganism an endogenous AKIII gene of that microorganism or an AKIII enzyme defined as follows:
(i) an AKIII encoded by all or part of a nucleotide sequence as set forth in SEQ ID NO. 3 or by a nucleotide sequence having at least 50% identity to SEQ ID NO. 3 (or more particularly at least 55, 60, 65, 70 or 75% sequence identity to SEQ ID NO. 3) or a nucleotide sequence which hybridises with the complement of SEQ ID NO. 3 under high stringency conditions (0.1×SSC, 0.1% SDS, 65° C., and wash conditions: 2×SSC, 0.1% SDS, 65° C., followed by 0.1×SSC, 0.1% SDS, 65° C.) or a nucleotide sequence which is degenerate with the nucleotide sequence of SEQ ID NO. 3; or
(ii) an AKIII comprising all or part of the amino acid sequence as shown in SEQ ID NO. 4 or of an amino acid sequence which has at least 50% sequence identity with the amino acid sequence of SEQ ID NO. 4 (or more particularly at least 55, 60, 65, 70, 75 or 80% sequence identity to SEQ ID NO. 4).

The method of this aspect of the invention is thus a method in which the desired microorganism which over expresses the AKIII enzyme is cultured or grown using any desirable carbon source/substrate under conditions in which lysine may be produced. The microorganism may be modified to over-express AKIII by introducing into the host cell a nucleic acid molecule comprising a nucleotide sequence as defined above, or encoding an AKIII as defined above. The microorganism may then be cultured or grown under conditions in which the nucleotide sequence is expressed. In another aspect, the present invention provides a microorganism which overexpresses an endogenous AKIII gene of that microorganism or an AKIII enzyme defined as follows:
(i) an AKIII encoded by all or part of a nucleotide sequence as set forth in SEQ ID NO. 3 or by a nucleotide sequence having at least 50% identity to SEQ ID NO. 3 (or more particularly at least 55, 60, 65, 70 or 75% sequence identity to SEQ ID NO. 3) or a nucleotide sequence which hybridises with the complement of SEQ ID NO. 3 under high stringency conditions (0.1×SSC, 0.1% SDS, 65° C., and wash conditions: 2×SSC, 0.1% SDS, 65° C., followed by 0.1×SSC, 0.1% SDS, 65° C.) or a nucleotide sequence which is degenerate with the nucleotide sequence of SEQ ID NO. 3; or (ii) an AKIII comprising all or part of the amino acid sequence as shown in SEQ ID NO. 4 or of an amino acid sequence which has at least 50% sequence identity with the amino acid sequence of SEQ ID NO. 4 (or more particularly at least 55, 60, 65, 70, 75 or 80% sequence identity to SEQ ID NO. 4).

More particularly, this aspect of the invention provides a microorganism which has been modified to overexpress an AKIII gene or enzyme as defined above. In one particular embodiment, such modification includes introducing into said microorganism a nucleic acid molecule encoding an AKIII enzyme as defined above.

Thus such a nucleic acid molecule encodes a polypeptide having AKIII activity and may comprise or consist of a nucleotide sequence which is
(i) a nucleotide sequence as set forth in SEQ ID NO. 3;
(ii) a nucleotide sequence having at least 50% sequence identity, more particularly at least 50, 55, 60, 65, 70, 75, 77, 79, 80, 81, 83, 85, 86, 87, 88, 89, 90, 91, 93, 95, 97, 98 or 99% sequence identity, with a nucleotide sequence as set forth in SEQ ID NO. 3;
(iii) a nucleotide sequence that hybridises that the complement of SEQ ID NO. 3 under high stringency hybridisation conditions (0.1×SSC, 0.1% SDS, 65° C., and wash conditions: 2×SSC, 0.1% SDS, 65° C., followed by 0.1×SSC, 0.1% SDS, 65° C.);
(iv) a nucleotide sequence which is degenerate with the nucleotide sequence of SEQ ID No. 3;
(v) a nucleotide sequence which encodes a polypeptide having the amino acid sequence as set forth in SEQ ID NO. 4 or an amino acid sequence which has at least 50% sequence identity or preferably at least 50, 60, 65, 70, 75, 80, 82, 84, 86, 88, 90, 92, 94, 95, 96, 97, 98 or 99% sequence identity, with an amino acid sequence as set forth in SEQ ID NO. 4;
(vi) a nucleotide sequence which is a part of the nucleotide sequence of (i) or (ii) or (iv) or (v).

Parts of the nucleic acid molecules/nucleotide sequences and AKIII amino acid sequence are further defined below.

Thus, the microorganism which is modified (or "engineered") to over-express AKIII may contain an exogenously-introduced AKIII encoding nucleic acid molecule as defined above (the organism may be transformed with such an AKIII-encoding nucleic acid molecule). The nucleic acid molecule may encode an AKIII enzyme which is homologous or heterologous (i.e. native or non-native) to that host. Thus, a further copy (or more) of a gene which is native to the host may be introduced. The nucleic acid molecule which is introduced may comprise a nucleotide sequence derived from the native gene, or from a different source.

Alternatively, the "endogenous" AKIII of the producing micro-organism may be over-expressed. By "endogenous" is meant the AKIII which is produced as a result of expression of the endogenous AKIII-encoding gene in that microorganism (i.e. the gene which is present in that organism). Thus in this case an exogenous nucleic acid molecule encoding the AKIII is not introduced and only the gene sequence naturally present in the microorganism is expressed (although this may of course be modified e.g. by random or site-directed mutagenesis): It is possible to achieve over-expression by random mutagenesis and selection—a mutant may be obtained which over-expresses the native AKIII gene (the sequence of which is not modified or mutated). Thus microorganisms which over-express AKIII may be modified (e.g. by mutation) in such a manner such as to achieve over-expression of the native gene which is naturally contained in the genome of that organism (the sequence of which may or may not be modified). This may be for example by mutation of regulatory elements (e.g. promoters or other transcriptional or translational control elements or regulatory proteins etc) in the microorganism, which may for example lead to increased transcription of the native AKIII-encoding gene (e.g. yclM gene) of that organism.

As discussed above in relation to the first aspect of the invention, the AKIII which is over-expressed may be a variant of a wild-type or native sequence including a feedback inhibition-resistant mutant.

The producing microorganism may be any desired microorganism, eukaryotic or prokaryotic, but preferably it is a bacterium. More particularly it may be a bacterium included in, but not limited to, the following classes or genera: *Bacillus, Geobacillus, Methanomonas, Methylobacillus, Methylophilus, Pseudomonas, Protaminobacter, Methylococcus* and *Listeria*. The genus *Bacillus* is of particular interest and may specifically include, but, not be limited to *B. methanolicus, B. subtilis, B. amyloliquefaciens, B. clausii, B. cereus, B. halodurans*, B. sp. NRRL B-14911 and *B. licheniformis*.

It is preferred that the organism is thermotolerant or thermophilic, for example being capable of growth at 50-70° C. e.g. 50-60° C.

In a particularly preferred embodiment, the microorganism is, as noted above, *B. methanolicus*. The *B. methanolicus* or other microorganism in which the AKIII enzyme is over-expressed according to the invention can be any strain of the organism e.g. of *B. methanolicus*. Thus it can a native or wild-type strain or it can be a modified or mutant strain. The *B. methanolicus* or other microorganism can thus be of any genetic background including e.g. auxotrophs or mutants resistant to lysine analogues such as AEC. It will be readily appreciated that production of L-lysine may advantageously be further increased through use of the invention in a particular genetic background, e.g. in a strain in which L-lysine production is already elevated e.g. in an AEC-resistant strain or in a lysine over-producing mutant obtained by classical mutagenesis, or which has been engineered in other ways. However, as discussed above, the invention beneficially allows the use of wild-type microorganisms, specifically wild-type *B. methanolicus* as host strain, and this is represents one possible embodiment. Representative *B. methanolicus* strains include *B. methanolicus* MGA3. Other *B. methanolicus* wild type strains include: PB1 (NCIMB 13113), NOA2 (Schendel et al., (1990) supra), HEN9, TSL32, DFS2, CFS, RCP, SC6, NIWA, BVD, DGS, JCP, N2 (Brautaset et al., (2004) J. Bacteriol., 186(5): 1229-1238) and *B. methanolicus* mutant 13A52-8A66 (Hanson et al., (1996) Production of L-lysine and some other amino acids by mutants of *B. methanolicus*. In: Lidstrom et al., Microbial growth on C1 compounds. Kluwer Academic Publishers: Dordrecht, The Nederlands). As noted above, lysine over-producing mutants can be obtained by classical mutagenesis, as known or described in the art.

The AKIII may also be over-expressed in combination with the expression or over-expression of other genes in the microorganism. Such other genes may be other genes of the lysine biosynthetic pathway as shown in FIG. 1 e.g. asd, dapA, lysA. Lysine production may further be enhanced in this way, as shown in Example 2 below.

As referred to herein, "overexpressing" means that expression of the gene encoding the AKIII is increased as compared to, or relative to, the level of expression occurring in a microorganism which has not been modified according to the invention, e.g. the level of expression driven from the native AKIII-encoding (yclM) genomic (e.g. chromosomal) locus of the microorganism (e.g. *B. methanolicus*) (if it is a native AKIII expressor), or the level of expression seen in a control strain, e.g. a strain which has been modified as a control but which does not overexpress the AKIII gene (for example a strain containing any "empty" vector, or a vector with a control sequence). Gene expression is to be considered in terms of the amount of protein product (AKIII enzyme) produced, which may be determined by any convenient method known in the art. For example, expression can be determined by measuring protein activity (i.e. the activity of the expressed AKIII protein). Alternatively, the amount of protein produced can be measured to determine the level of expression, for example Western Blotting or other antibody detection systems, or indeed by any method of assessing or quantifying protein. Realtime PCR may also be used. The assay may be an in vivo or in vitro assay. Thus, expression (e.g. determined by detection of the specific activity of AKIII) may be 2-, 3- or 4-fold or more higher than that which results from the native (ie. endogenous) AKIII-encoding gene, but may be less in other systems or under other conditions.

AKIII activity may be determined by assaying for aspartokinase activity by procedures known in the art and described in the literature, for example as detailed in the Examples below. Thus, AK activity of an encoded protein can be determined by assaying for the formation of aspartyl hydroxamate from hydroxylamine as described by Black and Wright (Black et al., (1955) J. Biol. Chem., 213: 27-38).

According to the present invention "overexpressing" may mean simply that an additional AKIII gene is expressed in the host beyond the native AKIII gene (yclM) endogenously present in that host but is not limited to such a mechanism. It may include expressing an AKIII gene in an organism in which does not naturally contain such a gene.

As defined herein, overexpressing an AKIII enzyme may be by any means known in the art, such as by introducing a gene (or put more generally, a nucleic acid molecule comprising a nucleotide sequence) encoding an AKIII, e.g. a copy of the gene, for example expressed from a stronger or unregulated promoter relative to the native gene, and/or by introducing multiple copies of an AKIII-encoding nucleic acid molecule/gene.

The invention in one embodiment may thus provide a method wherein an AKIII gene is expressed which is not subject to transcriptional repression, e.g. by a product of the aspartate pathway or by a repressor of the endogenous AKIII gene.

The introduced gene(s) may be modified to render it relieved of transcriptional repression, e.g. by mutating or deleting recognition elements for transcriptional repressors or by using expression control elements (e.g. promoters) which are not subject to transcriptional regulation by the transcriptional regulator(s) which normally control expression of the AKIII gene, e.g. which control expression in its native situation, for example transcriptional repressors being products of the aspartate pathway. The endogenous AKIII-encoding gene may alternatively or additionally be modified in this way, or by addition of a stronger promoter. Thus, mutagenesis (including both random and targeted) may for example be used to mutate the endogenous control or regulatory elements so as to increase expression of the endogenous AKIII gene (e.g. increase transcription and/or translation). Alternatively, the organism may be engineered to introduce additional or alternative regulatory elements.

In a particular embodiment, an AKIII-encoding gene may be expressed from a non-native or heterologous promoter (that is a promoter which is heterologous to the AKIII-encoding gene, i.e. is not the native AKIII gene promoter) and particularly a strong, non-native or heterologous promoter. Thus, in this embodiment the AKIII-encoding gene is not used with its native promoter. An AKIII-encoding gene may be introduced which is under the control of a non-native promoter. As referred to herein, a strong promoter is one which expresses a gene at a high level, or at least at a higher level than effected by its native promoter. The term "strong promoter" is a term well known and widely used in the art and many strong promoters are known in the art, or can be identified by routine experimentation.

The use of a non-native promoter may advantageously have the effect of relieving the AKIII-encoding gene of transcriptional repression, as at least some of any repressive elements will be located in the native promoter region. By replacing the native promoter with a non-native promoter devoid of repressive elements responsive to the effects of pathway products, the AKIII-encoding gene will be at least partly relieved of transcriptional repression In a preferred embodiment the non-native promoter is native to *B. methanolicus*. Alternatively, said promoter is a methanol dehydrogenase (mdh) promoter.

In a particularly preferred embodiment, the non-native promoter is the methanol dehydrogenase (mdh) promoter of *B. methanolicus*. Other promoters functional in *B. methanolicus* include any of the promoters of known *B. methanolicus* genes. From the previously published sequence of pBM19 (Brautaset et al., (2004) supra) the following promoters have been experimentally characterized: glpX, fba, pfk, rpe promoters. From the previously published sequence of the hps+ phi operon (Brautaset et al., (2004) supra): hps promoter. For *Bacillus* generally any promoters from closely related species (e.g. bacilli) may be used. Promoters from other microorganisms which may be used both in *B. methanolicus* and other microorganisms are well known in the art and widely described in the literature.

Alternatively, an AKIII gene may be expressed using a native promoter. The invention encompasses the use of a microorganism which may endogenously express an AKIII gene (such as *B. methanolicus*) or which does not. In the case of the former, one or more additional copies of the native gene or a variant thereof or of another AKIII gene or encoding nucleic acid molecule may be introduced, and these may be introduced under the control of a native or non-native promoter. With a native promoter a multi-copy vector may for example be used. In the case of the latter, an AKIII gene (or encoding nucleic acid molecule) is introduced which is heterologous to that host, but which may be under the control of a promoter which is native or non-native to the AKIII gene from which the encoding nucleic acid molecule is derived.

As mentioned above, an increase in L-lysine production of up to 60-fold or more is obtainable by over-expression of wild-type *B. methanolicus* AKIII from the *B. methanolicus* mdh promoter in a wild-type *B. methanolicus* host, relative to a control lacking the exogenous AKIII construct. However, it will be appreciated that this may vary significantly, depending on the precise system used, and the "baseline" level of L-lysine production. Thus, an increase in L-lysine production of 60-, 70-, 80-, 90- or 100-fold, or more, may be attainable. Similarly, if the baseline level of L-lysine production is relatively high, e.g. in the context of a non-wild-type, L-lysine-producing background, the fold-increase obtainable may be less dramatic while remaining practically valuable. Accordingly, the increase in L-lysine production may be in the order of 2-, 3-, 4-, 5-, 6-, 7-, 8-, 9-, 10-, 12-, 15-, 20-, 25-, 30-, 40- or 50-fold, or more.

The present invention thus allows high increases in lysine production to be obtained, particularly when using a wild-type host where particularly high increases may be seen. It has further been surprisingly found that L-lysine exclusively is produced when AKIII, particularly the AKIII of *B. methanolicus* as disclosed herein, (or indeed AKI or AKII) is overexpressed in a microorganism. This is demonstrated in the Examples below in *B. methanolicus* using the *B. methanolicus* AKIII gene (yclM). As both L-threonine and L-methionine are also produced by the L-aspartate pathway, the sole synthesis of L-lysine by the methods of the invention was unexpected and could not have been predicted prior to the invention. Without wishing to be bound by theory, a possible explanation for the surprisingly high increase in L-lysine production according to the invention is that the AKIII, particularly the AKIII of *B. methanolicus*, may require both L-lysine and L-threonine for feedback inhibition. AKIII in *B. subtilis* has been reported as requiring both L-lysine and L-threonine for feedback inhibition (Schendel et al., (1992) supra). While *B. methanolicus* AKIII has not been purified and biochemically characterised, and so it cannot be said for certain that this is the case, if it is then in view of the surprising observation that L-lysine is exclusively produced by overexpression of the *B. methanolicus* AKs, including AKIII, it may be that feedback inhibition is not occurring despite the use of a wild-type yclM gene.

Methods for introducing genes or nucleic acid molecules are well known in the art and widely described in the literature and any desired method may be used. The gene (nucleic acid molecule) may thus be introduced using a vector, which may be an autononously-replicating vector or a vector which allows the gene (nucleic acid molecule) to be integrated into the host genome (e.g. chromosome). The gene (nucleic acid molecule) to be expressed may thus be introduced into an expression vector and the expression vector may then be introduced into the host cell. Methods for constructing expression vectors and introducing them into host cells are well known in the art. Conveniently, the gene encoding AKIII may be introduced using a plasmid vector and a host microorganism, e.g. *B. methanolicus* host, may be transformed with the plasmid e.g. by electoporation. Methods for introducing nucleic acids and vectors into microorganisms are well known and widely described in the literature. The choice of method may depend on the microorganism used. As described in Brautaset et al., 2007 (supra), methods for introducing genes into *B. methanolicus* and suitable plasmids etc for use in such methods are known and available in the art. Particular mention may be made of vectors based on the *E. coli-B. subtilis* shuttle plasmid pHP13 as described by Jakobsen et al., 2006 (supra). Reference may also be made to plasmids PDQ503, PDQ507, PDQ508, and PEN1 reported in Cue et al., 1997 (Appl. Environ. Microbiol., 63: 1406-1420). As exemplified herein, in the case of a *B. methanolicus* host the plasmid pTB1.9mdh which contains the mdh gene may conveniently be used as a vector for introduction of the gene under the control of the mdh promoter.

In order to produce lysine the host organism modified according to the present invention may be grown or cultured under conditions which allow lysine to be produced using a desired or appropriate substrate. The host cells may thus be grown in the presence of the substrate or source e.g. in growth media containing the substrate or to which the substrate has been added. Methods and conditions for growing *B. methanolicus* are known and described in the art, and are exemplified in Example 1 below. The substrate, or carbon source, which is used for lysine production may be any suitable substrate of choice and may depend on the microorganism which is used. Thus, suitable substrates may be any of the carbon-sources known and used in the art today e.g. poly- or monosaccharides (e.g. glucose, other hexose sugars, pentose sugars), acids (e.g. acetate), amino acids (e.g. glutamate), one-carbon compounds (e.g. methanol, methane) and complex raw-materials (e.g. molasses, protein hydrolysates). The substrate may be provided in purified or "isolated" form or as part of a crude, or unrefined or partially refined mixture, for example a by-product of another commercial or industrial process. In the case of a methylotroph such as *B. methanolicus* methanol may be used as substrate. However, *B. methanolicus* grows also on other substances, such as sugars, which may be used, e.g. mannitol, glucose, maltose, ribose, acetate, glutamate, α-ketoglutarate (Schendel et al, 1990, supra). Exemplified below is the use of mannitol as substrate for *B. methanolicus* engineered to over-express AKIII. It will be seen that high levels of lysine production may be achieved, exceeding even the lysine levels attainable using methanol.

As mentioned above, the instant invention has been made possible in part by the cloning, for the first time, by the present inventors of the genes encoding AKIII of *B. methanolicus*, yclM. The inventors have also cloned for the first time the gene encoding AKI of *B. methanolicus*, dapG. This had not previously been achieved, despite efforts which resulted in the identification of lysC, encoding AKII, of *B. methanolicus* (Schendel et al., (1992) supra). The nucleic acid sequence of *B. methanolicus* dapG and yclM are set forth in SEQ ID NOs: 1 and 3, respectively, whilst the amino acid sequence of the encoded proteins is shown in SEQ ID NOs: 2 and 4, respectively.

The invention therefore provides a nucleic acid molecule, preferably an isolated nucleic acid molecule, which encodes a polypeptide (or protein) having AK activity, comprising or consisting of a nucleotide sequence selected from the group consisting of:

(i) a nucleotide sequence as set forth in SEQ ID NO: 1 or 3, (ii) a nucleotide sequence having at least 80% sequence identity, more particularly at least 82, 84, 86, 88, 90, 92, 94, 95, 96, 97, 98 or 99% sequence identity with a nucleotide sequence as set forth in SEQ ID NO: 1, (iii) a nucleotide sequence having at least 75% sequence identity, more particularly at least 77, 79, 80, 81, 83, 85, 86, 87, 88, 89, 90, 91, 93, 95, 97; 98 or 99% sequence identity, with a nucleotide sequence as set forth in SEQ ID NO: 3, (iv) a nucleotide sequence that hybridizes with the complement of (i) under the following hybridisation conditions: 0.1×SSC, 0.1% SDS, 65° C., and wash conditions: 2×SSC, 0.1% SDS, 65° C., followed by 0.1×SSC, 0.1% SDS, 65° C. (high stringency conditions);

(v) a nucleotide sequence which is degenerate with the nucleotide sequence of SEQ ID No. 1 or 3;

(vi) a nucleotide sequence which is a part of the nucleotide sequence of SEQ ID NO. 1 or 3 or of a nucleotide sequence which is degenerate with the sequence of ID NO. 1 or 3;

(vii) a nucleotide sequence which is complementary to the nucleotide sequence of any one of (i) to (vi).

Alternatively stated, the invention provides a nucleic acid molecule, preferably an isolated nucleic acid molecule, which encodes a polypeptide having AK activity, comprising or consisting of a nucleotide sequence selected from the group consisting of:

(i) a nucleotide sequence encoding all or part of the polypeptide whose amino acid sequence is set forth in SEQ ID NO: 2 or 4;

(ii) a nucleotide sequence encoding all or part of a polypeptide which has an amino acid sequence having at least 90% sequence identity, preferably at least 92, 93, 94, 95, 96, 97, 98 or 99% sequence identity with an amino acid sequence as set forth in SEQ ID NO: 2;

(iii) a nucleotide sequence encoding all or part of a polypeptide which has an amino acid sequence having at least 80% sequence identity, preferably at least 82, 84, 86, 88, 90, 92, 94, 95, 96, 97, 98 or 99% sequence identity, with an amino acid sequence as set forth in SEQ ID NO. 4;

(iv) a nucleotide sequence which is complementary to the nucleotide sequence of any one of (i) to (iii).

The nucleic acid molecule preferably encodes a polypeptide or protein which is an AKI or an AKIII or a part thereof having AK activity.

Preferably, the nucleic acid molecule as defined in parts (i)-(v) or (i) to (iii) above (i.e. not including the "complementary" molecule of part (vi) or part (iv)), encodes a polypeptide or protein having or retaining the function or activity or properties of the AKI and AKIII enzymes as defined by the amino acid sequences of SEQ ID NOs 2 and 4.

The terms "polypeptide" and "protein" are used interchangeably herein and include any length of amino acid chain (i.e. any polymer or oligomer of amino acids).

As noted above, the invention extends to parts or functional fragments of the nucleotide sequences defined above, by which it is meant parts or fragments that encode a protein or polypeptide which has the same or substantially the same activity as the full length protein as defined above. Tests to determine whether a protein/polypeptide encoded by such a part or fragment has the same or substantially the same activity (e.g. catalytic or enzymatic activity) as the full length polypeptide/protein as defined above include those discussed above. Normally parts or functional fragments of nucleic acid molecules will only have small deletions relative to the full length nucleic acid molecule, e.g. deletions of less than 50, 40, 30, 20 or 10 nucleotides, for example at the 5' end encoding the N-terminus of the protein, the 3' end encoding the C-terminus of the protein or internally within the encoding region, although larger deletions e.g. of at least 60, 70, 80, 90, 100, 150, 200, 300, 400, 500, 600 or 700 nucleotides, or deletions of less than 60, 70, 80, 90, 100, 150, 200, 300, 400, 500, 600 or 700 nucleotides can also be carried out, if the fragment has the same or substantially the same activity (e.g. catalytic or enzymatic activity) as the full length protein as defined above. The activity of the encoded polypeptide or protein can readily be tested to determine whether it shares the same activity as the full length polypeptide or protein, e.g. as set out above.

Representative parts or fragments may comprise at least 50%, and preferably at least 60, 70, 75, 80, 85, 90 or 95% contiguous nucleotides of the nucleotide sequence as set forth in SEQ ID No. 1 or 3. Thus, for example in the case of the yclM sequence of SEQ ID No. 3, the part or fragment may be at least 684, 821, 957, 1026, 1094, 1163, 1231 or 1300 nucleotides long. In the case of the dapG sequence of SEQ ID No. 1, the part or fragment may be at least 621, 745, 869, 931, 994, 1056, 1118 or 1178 nucleotides long. Exemplary part or fragment sizes thus include at least 620, 700, 800, 850, 900, 950, 1000, 1050, 1100, 1150, 1200, 1250 and 1300 nucleotides.

Shorter fragments of the nucleic acid molecule of the invention can be used as probes, e.g. for PCR or hybridisation protocols. Shorter fragments can be e.g. 10-20, 30, 20-25 nucleotides in length. Such probes are useful in protocols for identifying further nucleic acid molecules which share homology with the nucleic acid molecules of the invention.

The term "nucleic acid molecule" as used herein refers to a polymer of RNA or DNA that is single or double stranded, optionally including synthetic, non-natural or altered nucleotide bases. Examples of such polynucleotides include cDNA, genomic DNA and dsRNA, inter alia. Preferably, the nucleic acid molecule is DNA.

Whilst the nucleic acid sequences referred to herein comprise thymidine ("t") nucleotides, it will be understood that the invention also relates to corresponding sequences wherein thymidine is replaced by uridine ("u").

The invention thus includes nucleic acid molecules which are variants of the nucleic acid molecules of SEQ ID No. 1 and 3, particularly functionally equivalent variants. The "variant" nucleic acid molecules may thus have single or multiple nucleotide changes compared to the nucleic acid molecules of SEQ ID Nos. 1 and 3. For example, the variants might have 1, 2, 3, 4, or 5 or more nucleotide additions, substitutions, insertions or deletions.

In a further aspect, the invention provides a protein (or polypeptide) having AK activity and comprising or consisting of a sequence of amino acids selected from the group consisting of:

(i) all or part of an amino acid sequence as set forth in SEQ ID NO: 2 or 4, (ii) all or part of an amino acid sequence having at least 90% sequence identity, preferably at least 92, 93, 94, 95, 96, 97, 98 or 99% sequence identity with an amino acid sequence as set forth in SEQ ID NO:2; and (iii) all or part of an amino acid sequence having at least 80% sequence identity, preferably at least 82, 84, 86, 88, 90, 92, 94, 95, 96, 97, 98 or 99% sequence identity with an amino acid sequence as set forth in SEQ ID NO: 4.

The protein or polypeptide preferably is an AKI or AKIII or a part thereof having AK activity. More particularly the part retains the function or activity of properties of the AKI or AKIII from which it derives (as defined by reference to the amino acid sequence of SEQ ID NOS. 2 and 4).

The protein or polypeptide may alternatively be defined with reference to, the encoding nucleic acid sequences and as such the protein or polypeptide of the invention can be encoded by any of the nucleic acid molecules of the invention, as described above.

The invention extends to functional parts or fragments of the full length protein molecules, by which it is meant parts or fragments which have the same or substantially the same activity as the full length proteins as defined above i.e. they should be considered to be functionally equivalent variants. As noted elsewhere herein, the property can be tested for in various ways in a straightforward manner. Normally these functional fragments will only have small deletions relative to the full length protein molecule, e.g. of less than 50, 40, 30, 20 or 10 amino acids, although as noted above in connection with nucleic acid molecules larger deletions e.g. of up to 60, 70, 80, 90, 100, 150, 200 amino acids or at least 60, 70, 80, 90, 100, 150, 200 amino acids, may be appropriate. In all cases, the fragments should have the same or substantially the same activity as the full length proteins as defined above i.e. they should be considered to be functionally equivalent variants. These deletions may be at the N terminus, the C terminus or they may be internal deletions.

Representative parts or fragments may comprise at least 50%, and preferably at least 60, 70, 75, 80, 85, 90 or 95% contiguous amino acids of the amino acid sequence as set forth in SEQ ID No. 2 or 4. Thus, for example in the case of the YclM sequence of SEQ ID No. 4, the part or fragment may be at least 227, 318, 341, 364, 387, 409 or 432 amino acids long. In the case of the DapG sequence of SEQ ID No. 2 the part or fragment may be at least 206, 248, 289, 310, 330, 351, 372 or 392 amino acids long. Exemplary part or fragment sizes thus include at least 200, 220, 230, 250, 300, 330, 350, 360, 370, 380, 390, 400, 410, 420 and 430 amino acids.

The protein of the invention as defined above thus include variants of the sequences of SEQ ID Nos. 2 and 4, e.g. sequences having certain levels of sequence identity to the recited sequences. Such variants could be naturally occurring variants, such as comparable proteins or homologues found in other species or more particularly variants found within other microorganisms, (which share the functional properties of the encoded protein as defined elsewhere herein).

Variants of the naturally occurring protein as defined herein can also be generated synthetically e.g. by using standard molecular biology techniques that are known in the art, for example standard mutagenesis techniques such as site directed or random mutagenesis (e.g. using gene shuffling or error prone PCR). Such mutagenesis techniques can be used to develop enzymes which have improved or different catalytic properties.

Derivatives of the protein as defined herein may also be used. By derivative is meant a protein as described above or a variant thereof which instead of the naturally occurring amino acid, contains a structural analogue of that amino acid. Derivatisation or modification (e.g. labelling, glycosylation, methylation of the amino acids in the protein) may also occur as long as the function of the protein is not adversely affected.

By "structural analogue", it is meant a non-standard amino acid. Examples of such non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4: 11-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are also useful for this purpose. Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9).

Multiple sequence alignments and percent identity calculations may be determined using the standard BLAST parameters, (using sequences from all organisms available, matrix Blosum 62, gap costs: existence 11, extension 1). Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

A further embodiment of the invention provides a construct comprising the isolated AKIII-encoding nucleic acid molecule of the invention (i.e. the nucleic acid of SEQ ID NO: 3 and related or derivative sequences as defined above) operably linked to a non-native promoter, particularly a strong, non-native promoter, preferably the mdh promoter of *B. methanolicus*. Optionally, the construct may additionally contain a further one or more genes, and/or one or more suitable regulatory sequences. The optional further one or more genes may be under the control of the same promoter as the AKIII-encoding nucleic acid molecule of the invention. The optional one or more of the regulatory sequences may be non-native regulatory sequences.

In the context of this invention, the term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e. the coding sequence is under the transcriptional control of the promoter). Coding sequences may be operably linked to regulatory sequences in sense or antisense orientation.

The term "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, operators, enhancers and translation leader sequences. As used herein, the term "promoter" refers to a nucleotide sequence capable of controlling the expression of a coding sequence or RNA. In general, a coding sequence is located 3' to a promoter sequence. Promoters may be derived in their entirety from a native gene, or be composed of different elements derived from different promoters found in nature, or even comprise synthetic nucleotide segments. It is further recognized that since in most cases the exact boundaries of regulatory sequences have not been completely defined, nucleic acid fragments of different lengths may have identical promoter activity.

A further embodiment of the invention provides a vector comprising a nucleic acid molecule or construct as defined above.

More particularly, vectors comprising the AKIII-encoding nucleic acid molecule of the invention (or construct of the invention) may be constructed. The choice of vector may be dependent upon the microorganism, the method that will be used to transform host cells, the method that is used for protein expression, or on another intended use of the vector. The skilled person is well aware of the genetic elements that must be present on the vector in order to successfully transform, select and propagate host cells containing the AKIII-encoding nucleic acid molecule or construct of the invention. The skilled person will also recognize that different independent transformation events will result in different levels and patterns of expression and thus that multiple events must be screened in order to obtain cells displaying the desired expression level and pattern. Such screening may be accomplished by Southern analysis of DNA, Northern analysis of mRNA expression, Western analysis of protein expression, inter alia.

The invention further provides a microorganism or host, particularly *B. methanolicus*, containing one or more of the nucleic acid molecules, constructs or vectors of the invention, particularly a nucleic acid molecule or a vector or construct comprising a nucleic acid molecule encoding AKIII which hence is capable of overexpressing AKIII. The host microorganism (e.g. *B. methanolicus*) may or may not endogenously contain an AKIII-encoding nucleic acid of the invention; in either case, it is genetically manipulated so as to alter the expression of AKIII. This can be achieved e.g. by introducing one or more further copies of the AKIII-encoding nucleic acid of the invention under the control of a non-native, preferably strong, promoter. In both of the above cases, genetic material is present in the host organism that is not present in naturally-occurring organism (i.e. exogenous genetic material is present).

In general, the exogenous genetic material is introduced using the process of transformation. Transformation will typically involve a plasmid or other vector which will also contain a marker (e.g. a gene) to enable identification of successfully transformed microorganisms, e.g. a gene for antibiotic resistance (for example against ampicillin). Other methods for selecting transformants are known to the skilled person and include the use of a light sensitive vector, a lux-gene, which causes positive colonies to light up in the dark. Other suitable vehicles for transformation of the bacteria include cosmids and bacteriophage molecules.

As noted above, the methods of the invention find particular utility in the commercial or industrial production of L-lysine. In a preferred aspect, therefore, the methods of producing L-lysine or of increasing expression of L-lysine relate to production-scale processes i.e. they are carried out on a production-scale or industrial scale, rather than a laboratory experiment. The processes may be preferred in a bioreactor or fermentor, particularly a production-scale bio-reactor or fermentor.

Figure 2:
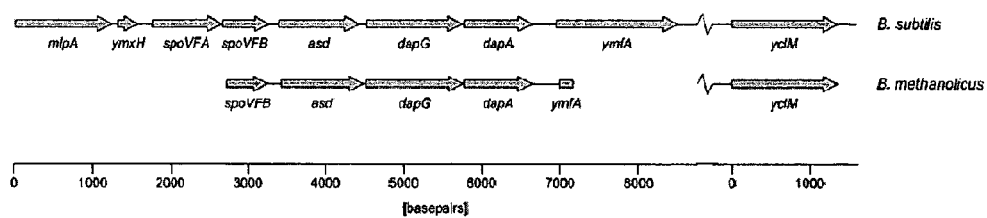
Figure 3:
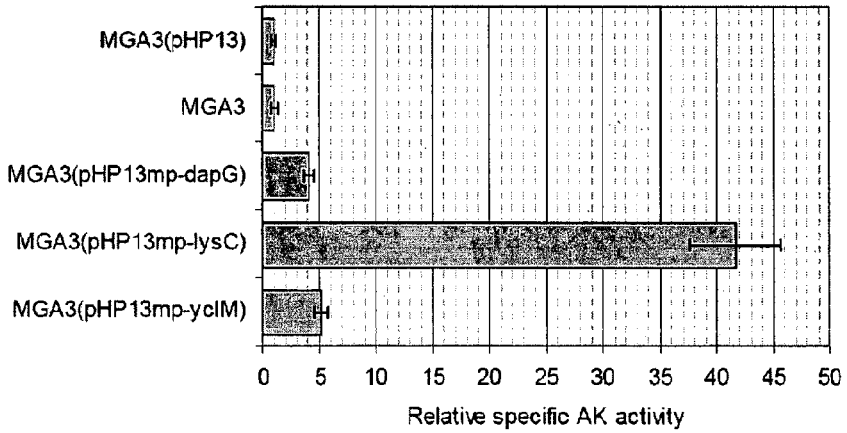
Figure 4:
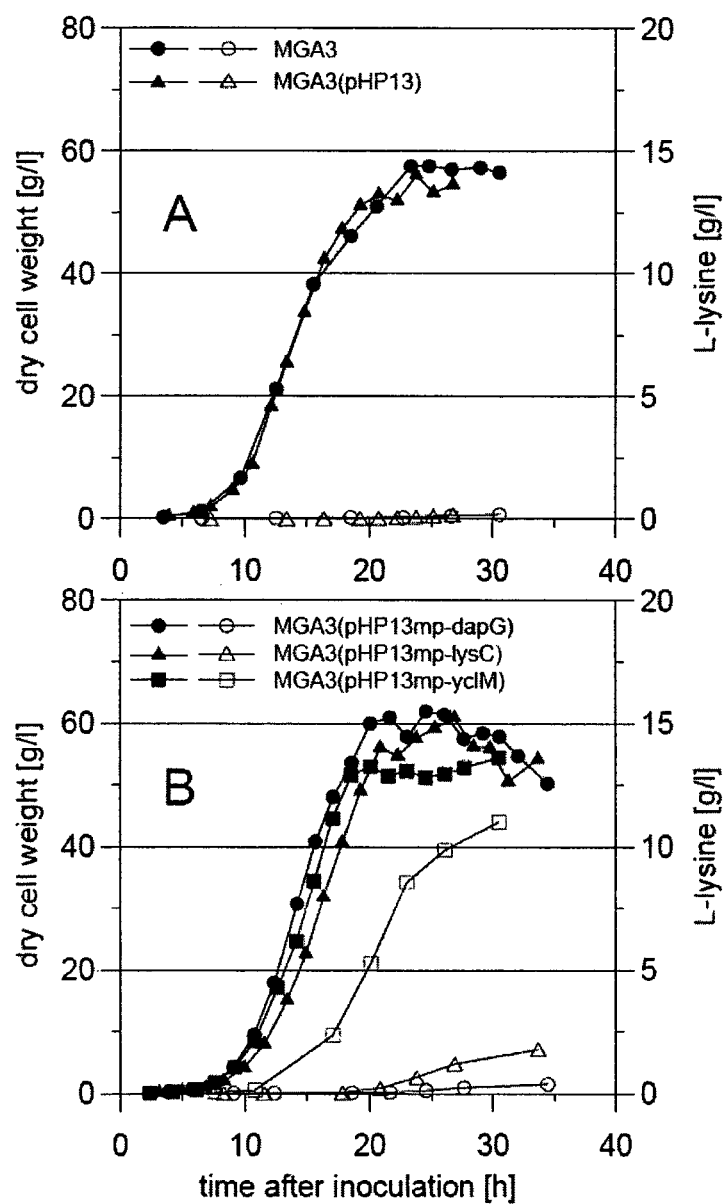

The invention will now be described in more detail in the following non-limiting Examples, in which:

FIG. 1 presents a general overview of the aspartate pathway (Paulus (1993) Biosynthesis of the Aspartate Family of amino acids. In: Sonenshein (Ed) *Bacillus subtilis* and other gram-positive bacteria: biochemistry, physiology and molecular genetics. American Society for Microbiology: Washington D.C.). The major metabolic functions of the end products are indicated in parentheses. *B. methanolicus* genes sequenced and presented in this work are underlined;

FIG. 2 shows the genetic organization of the partial dap operon and yclM of *B. methanolicus* MGA3 compared to the corresponding genes of *B. subtilis*;

FIG. 3 shows specific AK activity of crude extracts of shakeflask cultures of *B. methanolicus* MGA3 and recombinant strains overexpressing dapG, lysC and yclM. All specific enzyme activities are measured in vitro and are relative to that of the control-strain MGA3(pHP13) (defined as 1). The measured specific AK activity of MGA3(pHP13) was 0.05 U/mg protein; and FIG. 4 shows growth and L-lysine production in fermentation trials of: A, wild type MGA3 and the control strain MGA3(pHP13); B, recombinant MGA3-strains overexpressing dapG, lysC or yclM Filled symbols, dry cell weight; Empty symbols, L-lysine production (volume corrected values). Throughout the fermentations, the methanol level in the medium was kept at 150 mM by automatic feeding of methanol.

EXAMPLE 1

Materials and Methods

Biological Materials, DNA Manipulations and Growth Conditions

The bacterial strains and plasmids used in this study are listed in Table 1. *Escherichia coli* DH5a was used as a standard cloning host, and recombinant strains were grown at 37° C. in liquid or solid Luria-Bertani medium supplemented with chloramphenicol (15 ug/ml) when appropriate. Recombinant *E. coli* procedures were performed as described elsewhere (Sambrook et al., (1989) Molecular cloning: a laboratory manual. Cold Spring Harbor Laboratory Press: Cold Spring Harbor, N.Y.). Transformation of *B. methanolicus* was performed by electroporation as previously described (Jakobsen et al., (2006) supra).

For shakeflask cultures, *B. methanolicus* strains were grown at 50° C. in 100 ml MeOH$_{200}$ medium containing 200 mM methanol (Jakobsen et al., (2006) supra), and bacterial growth was monitored by measuring the optical density at 600 nm (OD$_{600}$).

Fermentations were performed in Applikon 3 l fermentors with an initial volume of 0.9 l. The medium, defined as UMN1 medium, contained K$_2$HPO$_4$, 4.09 g/l; NaH$_2$PO$_4$, 1.30 g/l; (NH$_4$)$_2$SO$_4$, 2.11 g/l; Yeast Extract (Difco), 0.25 g/l; d-Biotin, 6 mg/l; Vitamin B12, 0.01 mg/l; MgSO$_4$, 1 mM; Concentrated Metals Solution (Lee et al. 1996), 1 ml/l; Methanol, 150 mM. Chloramphenicol (5 µg/ml) was added when appropriate. Shakeflask cultures in MeOH$_{200}$ medium were used as inoculum and harvested at OD$_{600}$=1.1-1.3. The fermentors were inoculated with a culture volume equal to 75 ml divided by the OD$_{600}$ of the inoculum at time of harvest (1.1-1.3). Fermentations were run at 50° C. with initial agitation of 400 rpm and aeration of 0.5 VVM. The aeration was stepwise increased up to 1.0 VVM and the air was stepwise enriched up to 60% O$_2$, as oxygen demand increased. At all times, the dissolved oxygen was maintained at 30% saturation by automatic adjustment of the agitation speed up to 2,000 rpm. pH was maintained at 6.5 by automatic addition of 12.5% (w/v) NH$_3$ (typically 200-250 ml). Antifoam (Sigma Antifoam 204) was added to an initial concentration of 0.005% (v/v), and added on demand throughout the fermentation (typically 3 ml). The methanol concentration in the fermentor was monitored by online analysis of the head space gas by a mass spectrometer (Balzers Omnistar GSD 300 02). The head space gas was carried from the fermentor to the mass spectrometer in insulated stainless steel tubing heated to 60° C., with a flow rate of about 30 ml/min. The methanol concentration in the medium was maintained at 150 mM by automatic addition of MeOH Feed. Solution on methanol demand. MeOH Feed Solution contains 50 ml CKNFD Trace Metals per liter methanol. CKNFD Trace Metals contains MgCl$_2$, 344 mM; FeCl$_2$, 78.5 mM; MnCl$_2$, 50.5 mM; CuCl$_2$, 1.53 mM; CoCl$_2$, 1.60 mM; Na2MoO$_2$, 1.57 mM; ZnCl$_2$, 3.23 mM; HCl, 100 ml/l. Dry cell weight was calculated based on a conversion factor of 0.31 g/l dry cell weight per OD$_{600}$ (calculated as an average value based on measurements of OD$_{600}$ and dry cell weight of the reported fermentation trials). Specific growth rate was calculated by linear regression of semilogarithmic plots of biomass concentration vs. time based on data-points from the period of exponential growth (biomass concentration less than 15 g/l). The fermentations were run until the CO$_2$ content of the exhausted gas was close to zero (no cell respiration).

Due to significant increase of culture volume throughout the fermentation, all biomass and amino acid concentrations have been corrected for volume increase and subsequent dilution by multiplying measured concentration with the culture volume at sampling divided by the original culture volume. The correction factors used for end-point samples are between 1.5 and 1.7, and actual concentrations of amino acids and biomass measured in the bioreactors are therefore accordingly lower.

TABLE 1

Bacterial strains and plasmids

| Strain or plasmid | Description[a] | Reference |
|---|---|---|
| *B. methanolicus* | | |
| MGA3 | Wild-type strain | Schendel et al. 1990 |
| *E. coli* | | |
| DH5α | General cloning host | Bethesda Research Laboratories |
| Plasmids | | |
| pTB1.9mdhL | *E. coli* - *B. methanolicus* shuttle vector pTB1.9 carrying the mdh gene; Amp[r] Neo[r] | Brautaset et al. 2004 |
| pHP13 | *E. coli* - *B. methanolicus* shuttle vector; Clm[r] | Haima et al. 1987; Jakobsen et al. 2006 |
| pHP13mp-dapG | pHP13 carrying the dapG coding region under control of mdh promoter | This study |
| pHP13mp-lysC | pHP13 carrying the lysC coding region under control of mdh promoter | This study |
| pHP13mp-yclM | pHP13 carrying the yclM coding region under control of mdh promoter | This study |

[a]Amp[r], ampicillin resistance; Neo[r], neomycin resistance; Clm[r], chloramphenicol resistance.

Measurement of Amino-Acids and Ammonia

Amino-acids were quantified according to Skjerdal et al., 1996 (Appl. Micro. Biotechnol., 44(5): 635-642), using a buffer containing 0.02 M Na-acetate and 2% tetrahydrofuran, pH 5.9. Estimation of intracellular amino-acid concentration was performed as previously described (Brautaset et al., (2003) Appl. Environ. Microbiol., 69(7): 3986-3995), based on determination of the amino-acid content in a briefly washed and lysed cell culture, theoretical estimation of the intracellular volume, and an experimentally determined conversion factor of $2.2 \times 10^8$ cells/ml per $OD_{600}$. Ammonia was measured with Spectroquant Ammonium-Test Kit (Merck), according to the manufacturer's instructions (the samples were diluted 1:1 000 and 1:10 000 before analysis).

PCR-Assisted Cloning of *B. methanolicus* asd, dapG, dapA and lysC Genes

The putative AKI and AKIII encoding genes were PCR amplified from *B. methanolicus* MGA3 total DNA by using degenerated primers based on DNA sequences of yclM, mlpA, asd, dapG, and ymfA of *B. licheniformis*, *B. halodurans*, *B. cereus*, *Listeria innocua*, *L. monocytogenes* and *B. subtilis* (GenBank accession numbers AE017333, BA000004, NC_004722, AL592022, AL591824 and AL009126, respectively). DNA fragments of MGA3 covering asd, dapG and dapA were PCR amplified as overlapping fragments by using primer pairs (Table 2) mlpA-PPS-1F together with asd-PPS-1R (yielding a 3.9 kb fragment) and asd-PPS-1F together with ymfA-PPS-1R (yielding a 3.3 kb fragment). These fragments were sequenced by primer walking.

A central region of yclM was PCR amplified and partly sequenced by using degenerated primers based on conserved regions within yclM. Total DNA of MGA3 was digested with EcoRI, followed by heat inactivation of the restriction enzyme. The material was diluted and ligated for 72 hours at 4° C. Primers yclM-PPS-1F and yclM-PPS-1R, both pointing outwards from the previously PCR amplified yclM region were used to PCR amplify a 3 kb DNA fragment using the ligation mixture as template. This DNA fragment was sequenced by primer walking.

Construction of Vectors

DNA fragment A including the methanol dehydrogenase (mdh) coding region was PCR amplified from pTB1.9mdhL by using primers mdh-CDS-F1 and pTB1.9-R1. The putative mdh promoter region was PCR amplified from the same template by using primers mdh-prom-F1 and mdh-prom-R1, yielding DNA fragment B. pTB1.9mdhL was digested with PstI and BamHI and the vector backbone fragment was ligated with BamHI/Pcil-digested DNA fragment B and Pcil/PstI-digested DNA fragment A. Two Pcil sites were removed from the resulting vector by PCR amplification of the vector as two fragments: Fragment 1 using primers mp-mdh-P2-F1 and mp-mdh-P2-R2, and Fragment 2 using primers mp-mdh-P2-F2 and mp-mdh-P2-R1. The two fragments were end digested with SphI and KpnI and ligated to yield pTB1.9mp-mdh, which carries a Pcil-site between the mdh upstream and coding regions for simplified fusion of coding regions to the mdh promoter. Insertion of the Pcil site changed the four nucleotides upstream the mdh start codon from the original AAGA to CAM.

The coding regions of dapG, lysC and yclM were PCR amplified from *B. methanolicus* MGA3 total DNA by using primers dapG-CDS-F1 and dapG-CDS-R1, lysC-CDS-F1 and lysC-CDS-R1, yclM-CDS-F1 and yclM-CDS-R1, respectively. The resulting PCR fragments which all carried a Pcil site partly overlapping a GTG start codon were end-digested with Pcil and KpnI and used to replace the mdh coding region of pTB1.9mp-mdh, yielding vectors pTB1.9mp-dapG, pTB1.9mp-lysC and pTB1.9mp-yclM, respectively. In this process, the original ATG start codons of dapG and yclM were changed to GTG. A PstI/EcoRI fragment of pTB1.9mp-lysC including mdh promoter and lysC coding region was inserted into the corresponding sites of pHP13, yielding pHP13mp-lysC (7.3 kb). lysC coding region of pHP13mp-lysC was exchanged with dapG and yclM coding regions by inserting a PstI/KpnI fragment of pTB1.9mp-dapG and a SpeI/KpnI fragment of pTB1.9mp-yclM into the corresponding sites of pHP13mp-lysC, yielding pHP13mp-dapG (7.1 kb) and pHP13mp-yclM (7.2 kb), respectively.

TABLE 2

PCR primers used in this study

| Primer | Sequence (5'-3')[a] | |
|---|---|---|
| mlpA-PPS-1F | TCTACCTTCGTTGAGGAAGA | (SEQ ID NO: 10) |
| asd-PPS-1R | CACTCCTGAACGGTTAATCC | (SEQ ID NO: 11) |
| asd-PPS-1F | TGAGCAGACAAGAGCGATTA | (SEQ ID NO: 12) |
| ymfA-PPS-1R | ATAGATCGCTCCGATATGGT | (SEQ ID NO: 13) |
| yclM-PPS-1F | CCTGTGATCGGAATTGCAAGTGATAAAGGATTCTG | (SEQ ID NO: 14) |

TABLE 2-continued

PCR primers used in this study

| Primer | Sequence (5'-3')[a] | |
|---|---|---|
| ycIM-PPS-1R | ATCTTCGTTCCAGGAGCCGATGGATTATTGGTGTT | (SEQ ID NO: 15) |
| mdh-CDS-F1 | TCGACATGTGACAACAAACTTTTC | (SEQ ID NO: 16) |
| pTB1.9-R1 | ACGCATACCATTTTGAACGATGACC | (SEQ ID NO: 17) |
| mdh-prom-F1 | GCCGGATCCTGCAGTTCATTAAAGAGCAGC | (SEQ ID NO: 18) |
| mdh-prom-R1 | CGCGACATGTACTACCTCCTATTTATG | (SEQ ID NO: 19) |
| mp-mdh-P2-F1 | CGCGGCATGCGTTTCAATGAAGATCC | (SEQ ID NO: 20) |
| mp-mdh-P2-R1 | TTAAGCATGCAAAAGGCCAGGAACCG | (SEQ ID NO: 21) |
| mp-mdh-P2-F2 | TTTTGGTACCCGCCATAGGTCTAGAG | (SEQ ID NO: 22) |
| mp-mdh-P2-R2 | GGGCGGTACCTTATTCTTTAGTCTATC | (SEQ ID NO: 23) |
| lysC-CDS_F1 | CCGAACATGTGGGATTAATTGTCC | (SEQ ID NO: 24) |
| lysC-CDS_R1 | TTCCGGTACCCAGCAAATTGAACAGC | (SEQ ID NO: 25) |
| dapG-CDS-F1 | GCGCACATGTGAAAATTATCGTTCAAAAATTCGG | (SEQ ID NO: 26) |
| dapG-CDS-R1 | GCTAGGTACCGCTCCTCCTCATTCTATC | (SEQ ID NO: 27) |
| ycIM-CDS-F1 | GCGCACATGTGAAAGTAGCGAAGTTTGGAGGTTCTTC | (SEQ ID NO: 28) |
| ycIM-CDS-R1 | GCTAGGTACCAGTGTTTCACACCCAAATTCG | (SEQ ID NO: 29) |

[a]The underlined nucleotides are restriction sites used for simplified cloning of PCR products.

Preparations of Crude Cell Extracts and AK Assay

Crude cell extracts were prepared based on the protocol described by Brautaset et al., 2004 (supra). *B. methanollcus* cells were grown in $MeOH_{200}$ medium to exponential phase ($OD_{600}$=1.9-2.1) and 20 ml cell culture was harvested by centrifugation (3,200×g, 10 min, 10° C.). The supernatant was discarded and the cells were resuspended in 20 ml High Salt Buffer (the salt buffer of $MeOH_{200}$ medium at IX concentration, pH 7.2). 3 ml of the resuspended culture was centrifuged (3,200×g, 10 min, 10° C.), the supernatant was discarded and the pellet was frozen and stored at −20° C. The cells were thawed on ice, resuspended in 3 ml AK assay buffer (50 mM potassium phosphate, 10 mM $MgSO_4$, pH 7.5) and sonicated for 3 min (Branson Sonifier 250, output control 3, 30% duty cycle). Cell debris was removed by centrifugation (3,200×g, 20 min, 4° C.), and the supernatant was collected as crude cell extract and stored on ice for subsequent enzyme activity and total cell protein analysis. AK activity was determined by formation of aspartyl hydroxamate from hydroxylamine (Black et al., (1955) supra). The reaction mixture contained 400 µl Reaction buffer (0.5M Tris-HCl, 2M KCl, pH 8.0), 200 µl hydroxylamine solution (2M hydroxylamine, pH 8.0), 100 µl AAM solution (0.1M L-aspartic acid, 0.1M ATP, 0.1M $MgCl_2$, 0.2M Tris-HCl, pH 8.0) and 300 µl sample diluted in AK assay buffer. The reaction mixture was incubated at 50° C. for 20 min before the reaction was terminated by addition of 1 ml Fe solution (10% (w/v) $FeCl_3$, 3% (v/v) trichloracetic acid in 0.7M HCl, sterile-filtered before use). Formation of aspartyl hydroxamate was immediately measured at 540 nm using a spectrophotometer (Shimadzu, UV 1700). Assays in which the sample was replaced with standards of aspartyl hydroxamate were performed to correlate absorbance to aspartyl hydroxamate concentration. One unit of AK activity was defined as the amount of enzyme needed to produce 1 µmole aspartyl hydroxamate per minute under the above conditions (Black et al., (1955) supra). Protein concentrations were determined by the method of Bradford (Bio-Rad), using bovine serum albumin as a standard. AK assays were done in triplicates and four parallels were performed for each protein concentration measurement. The uncertainty of specific AK activity was calculated using the General Formula for Error Propagation (Taylor (1997) An introduction to error analysis: the study of uncertainties in physical measurements. University Science Books Sausalito, Calif. Section 3.11) based on average values and standard deviations of measured AK activities and protein concentrations.

Results yclM Encodes a Putative AKIII in *B. methanolicus*

Based on amino acid sequence alignments a set of degenerate primers were designed (see MATERIALS AND METHODS) and used to PCR amplify a 2 kb DNA fragment using MGA3 total DNA as a template. A putative yclM gene was successfully PCR amplified from MGA3 total-DNA using this strategy. A 2012 bp DNA fragment was sequenced and was found to contain the expected coding region and 605 bp of upstream sequence (FIG. 2). The deduced primary sequence (455 amino acids) of the yclM gene product exhibits the overall highest identity at the amino acid level to *B. licheniformis* AKIII (74%) and is 71% identical to AKIII *B. subtilis* str. 168, for which AK activity was experimentally verified (Kobashi et al., (2001) Biosci. Biotechnol. Biochem., 65(6): 1391-1394). It has low primary sequence identity to both AKI and AKII of *B. subtilis* (23% and 25%, respectively). Together, these data suggests that the *B. methanolicus* yclM gene encodes a putative AKIII isozyme.

asd, dapG and dapA Encoding Putative Aspartate Semialdehyde Dehydrogenase, AKI and Dihydrodipicolinate Synthase, Respectively, are Organized in a Putative dap Operon in *B. methanolicus*

In *B. subtilis*, asd, dapG and dapA are located within the dap operon (Chen et al., (1993) J. Biol. Chem., 268(13): 9448-9465). By aligning known sequences of several related species (see MATERIALS AND METHODS), we noted a conserved organization of genes upstream of, inside and downstream of the dap operon, and we hypothesized that this genetic organization was similar in *B. methanolicus* as in the examined related species. By using degenerated primers based on conserved regions within mlpA, asd, dapG and ymfA (FIG. 2), we PCR amplified overlapping DNA fragments covering a partial, putative MGA3 dap operon. Totally, a DNA region of 4465 bp was sequenced comprising the putative genes asd, dapG and dapA, in addition to parts of the upstream putative spo VFB and downstream putative ymfA (FIG. 2). The deduced gene products of asd, dapG and dapA (351, 413 and 290 amino acids, respectively) display the highest primary sequence identities to aspartate semialdehyde dehydrogenase, AKI and dihydrodipicolinate synthase of *Bacillus* sp. NRRL B-14911 (76, 85 and 79%, respectively). The deduced dapG gene product is 68% identical to the AKI of *B. subtilis* str. 168, for which AK activity was experimentally verified (Chen et al., (1993) supra), while the primary sequence identity to AKII and AKIII of *B. subtilis* is low (38% and 24%, respectively). This suggests that the *B. methanolicus* dapG gene encodes a putative AKI isozyme.

The organization of asd, dapG and dapA with equal orientation and short intergenic regions (31 and 14 nucleotides, respectively) is similar to that of *B. subtilis* (FIG. 2), where these three genes are transcribed as one unit during vegetative growth (Chen et al., (1993) supra). The short intergenic regions of the putative MGA3 dap operon, do not allow obvious mRNA secondary structure formation. This seems to be in contrast to two potential secondary structures of the 91 nucleotide long asd-dapG intergenic transcript of *B. subtilis*. These secondary structures have been suggested to differ in the availability of the dapG ribosome binding site for interaction with 16S ribosomal RNA, and represent a possible mechanism to down-regulate dapG-dapA expression relative to asd (Chen et al., (1993) supra).

Construction of a Cassette Cloning and Expression System for *B. methanolicus*

We constructed a cassette expression system as a tool for simplified gene overexpression in *B. methanolicus* based on mdh and the *E. coli-B. methanolicus* shuttle vector pHP13 (Brautaset et al., (2004) supra; Jakobsen et al., (2006) supra). By introducing a unique restriction site partly overlapping the mdh start codon and unique restriction sites downstream the coding region, this cassette system offers a simple cloning strategy for the in-frame fusion of any coding region to the mdh promoter region and ribosome binding site.

Recombinant Expression of dapG and YclM Confirms that they Encode AK Activity

For overexpression of AK genes in *B. methanolicus*, we established the expression vectors pHP13mp-dapG, pHP13mp-lysC and pHP13mp-yclM, in which the genes dapG, lysC and yclM are under control of the mdh promoter and ribosome binding site. Thus, in these constructions, the AK-encoding genes are released from any original transcription regulation by products of the aspartate pathway. These expression vectors were introduced into the wild type MGA3, and we established MGA3(pHP13) as a control strain. We compared AK activity in crude extracts prepared from MGA3 and the recombinant strains grown in shakeflasks in defined methanol medium. The results (FIG. 3) show that crude extracts of the recombinant strains overexpressing putative AKI and AKIII (encoded by dapG and yclM, respectively) and AKII (encoded by lysC) exhibit four to forty-fold higher specific AK activities in vitro than that of the control strain. These results confirm the deduced biochemical function of dapG and yclM gene products. As expected, the wild type strain MGA3 and the control strain MGA3(pHP13) express similar AK activities. Interestingly, lysC overexpression gave 10-fold higher in vitro AK activity compared to dapG and yclM. Whether this is due to a higher expression level or different biochemical properties of the AK proteins measured in vitro is unknown. For all samples, a similar in vitro specific activity could be measured at different dilutions of the crude extract (data not shown), indicating that feedback regulation did not affect the results of the enzyme assay.

Overexpression of dapG, lysC and yclm Leads to Increased L-Lysine Production in *B. methanolicus* MGA3

In order to evaluate the effect of increased expression of dapG, lysC and yclM on L-lysine production in wild type *B. methanolicus*, we ran high cell density fed batch fermentation trials in defined methanol medium with the established recombinant strains. Amino acid production (defined as amount of amino acid secreted to the growth medium) was monitored throughout the fermentations. To compare different bioreactor trials, all biomass concentrations and amino acid production reported herein have been corrected for dilution caused by feeding throughout the fermentation (see MATERIALS AND METHODS).

Under the conditions tested, the wild type MGA3 reached a maximum biomass concentration of 58 g/l in 23 hours with an initial specific growth rate of 0.49 $h^{-1}$. The final L-lysine production of MGA3 was 0.18 g/l, in agreement with previous results (Schendel et, al., (1990) supra; Brautaset et al., (2003) supra). The control strain MGA3(pHP13) was similar to the wild type in respect to both specific growth rate, maximum cell density and L-lysine production, indicating that pHP13 cause no effects on these properties (FIG. 4 and Table 3). Interestingly, all the recombinant strains overexpressing either dapG, lysC or yclM produced more L-lysine than the control strain, and retained a similar specific growth rate (Table 3). The most dramatic effect on L-lysine production was observed with strain MGA3(pHP13mp-yclM), which produced over 60-fold more L-lysine (11 g/l) than the control strain (FIG. 4 and Table 3). The recombinant strains overexpressing dapG and lysC displayed a 2-fold and 10-fold increase in L-lysine production, respectively. All strains were similar with respect to L-glutamate production (48-52 g/l), and the production of the other end products of the aspartate pathway, L-methionine (<0.5 g/l) and L-threonine (<0.1 g/l) remained low. To verify reproducibility of the fermentation trials, MGA3(pHP13) and MGA3(pHP13mp-yclM) were run twice in independent fermentation trials. Optical density and amino acid concentration varied less than 10% between the parallel fermentation trials at any sampling point, and calculated specific growth rate did not vary more than +/−0.02 $h^{-1}$.

TABLE 3

Initial specific growth rate, maximum dry cell weight and
final L-lysine production of B. methanolicus wild type MGA3 and
recombinant strains overexpressing dapG, lysC and yclM.

| Strain | Specific growth rate [h$^{-1}$] | Dry cell weight [g/l][1] | L-lysine production [g/l][1] | L-lysine in growth medium [g/l][2] |
|---|---|---|---|---|
| MGA3 | 0.49 | 58 | 0.18 | 0.12 |
| MGA3(pHP13) | 0.49 | 56 | 0.18 | 0.12 |
| MGA3(pHP13mp-dapG) | 0.50 | 62 | 0.38 | 0.23 |
| MGA3(pHP13mp-lysC) | 0.46 | 61 | 1.8 | 1.1 |
| MGA3(pHP13mp-yclM) | 0.50 | 54 | 11 | 7.0 |

[1]Reported biomass and L-lysine production are corrected for dilution caused by feeding throughout the fermentation in order to compare results from different bioreactor trials (see Materials and Methods).
[2]L-lysine concentration measured in growth medium (no volume correction).

EXAMPLES 2 AND 3

Materials and Methods

Additional information not already described in the Materials and Methods of Example 1.
DNA Manipulations and Growth Conditions
General cloning, PCR, DNA sequencing and fermentations were performed as already described in Example 1. *B. methanolicus* growth on mannitol was done used by using Mann$_{20}$ medium which is equal to 2× Mann$_{10}$ as described in Jakobsen et al., (2006) J Bacteriol., 188(8): 3063-3072.
Measurement of L-Lysine
Measurements of L-lysine were performed by using HPLC as described in Example 1.
Real-Time PCR
*B. methanolicus* cultures were grown to late logarithmic phase (OD$_{600}$=3), before harvesting. Cell lysis including RNA protection, isolation of total RNA, and concomitant cDNA synthesis was performed as described elsewhere (Jakobsen et al., 2006, supra). Total RNA concentrations were quantified using a NanoDrop® ND-1000 Spectrophotometer (NanoDrop Technologies). Primers for the real-time PCR experiments we designed by using the computer software Primer ExpressR v 2.0 (Applied Biosystems). Detection of PCR products was performed with the ABI 7500 System (Applied Biosystems) under the following profiles. For the primer efficiency test, reaction mixtures were incubated at 95° C. for 10 min to activate hot-start Taq polymerase followed by a two-step PCR protocol (denaturation for 15 sek at 95° C. followed by a combined annealing—extension step (with fluorescent data acquisition) for 1 min at 60° C.). This step was repeated in 40 cycles. The determination of the dissociation temperature was performed by a subsequent cycle with 15 sek at 95° C., 1 min at 60° C. and a final step at 95° C. for 15 sek. For the real-time quantitative PCR comparative studies, the profile was reduced to the steps used for the primer efficiency test. Data acquisition and analysis were performed with the Sequence Detection software version v1.2.3 (Applied Biosystems Inc.) under standardized reaction with SYBR signal.
Construction of Expression Vectors
pTH1mp-lysC:
Plasmid pHP13 (Jakobsen et al., 2006, supra) was digested with PciI, and the resulting cohesive ends were blunted by using T4 DNA Polymerase, and the ends religated to yield plasmid pTH1. Plasmid pHP13mp-lysC (Example 1) was digested with PstI/EcoRI and the 2.6 kb fragment was isolated and ligated into the corresponding sites of pTH1, yielding the cassette cloning an expression vector pTH1mp-lysC. This vector is analogous to the plasmid HP13mp-lysC and has a unique PciI site for one-step cloning of any coding gene downstream of the strong mdh promoter and in-frame with the mdh rbs region.
PTH1mp-asd, pTH1mp-dapA, and pTH1mp-lysA
DNA fragments with the coding regions of asd (1117 bp), dapA (904 bp), and lysA (1322 bp) were PCR amplified from *B. methanolicus* total DNA by using the following primer pairs:

```
asd-F:
                                        (SEQ ID NO: 30)
5'-GCGCACATGTGGGTCAAGAAAATGGTCTTC-3' asd-R:
                                        (SEQ ID NO: 31)
5'-ATGGTACCTGCCCCCGAATTTTTGAAC-3' dapA-F:
                                        (SEQ ID NO: 32)
5'-GCGCACATGTGGTTTCATTTGGTCGAATATC-3' dapA-R:
                                        (SEQ ID NO: 33)
5'-ATGGTACCGGCAGTAAAAACTCCATTGAT-3' lysA-F:
                                        (SEQ ID NO: 34)
5'-GCGCACATGTGTATTTTCATGGCACAACA-3' lysA-R:
                                        (SEQ ID NO: 35)
5'-ATGGTACCGCAGCTTAGTATCTTACTCT-3'
```

PciI and KpnI restriction sites are underlined in the forward and reverse primers, respectively. The obtained PCR products were end digested with PciI/KpnI and ligated into the corresponding sites of pTH1mp-lysC (substituting the lysC gene), yielding expression vectors pTH1mp-asd, pTH1mp-dapA, and pTH1mp-lysA, respectively. The inserts in all plasmids were verified by DNA sequencing.
pHP13mp-yclM+1 ysA
Plasmid pTH1mp-lysA was digested with SpeI/NcoI and the 1.8 kb fragment was ligated into vector pHP13mp-yclM digested with XbaI/NcoI, yielding plasmid pHP13mp-yclM+lysA.
pTH1mp-dapA+yclM
Plasmid pHP13mp-yclM was digested with SpeI/NcoI and the 1.9 kb fragment was purified and ligated into pTH1mp-dapA XbaUNcoI sites, yielding expression vector pTHmp-dapA+yclM.
The vectors were transformed to *B. methanolicus* strain MGA3 by electroporation.

EXAMPLE 2

Overexpression of Additional *B. methanolicus* Genes by Using pHP13 and the mdh Promoter and the Effects on L-Lysine Production Overexpression of the three different AK encoding genes (dapG, lysC, and yclM) and the effects on L-lysine production in MGA3 (wild-type *B. methanolicus*) tested in fermentors, is described in Example 1. In a further study additional genes of the L-lysine biosynthetic pathway have been overexpressed using the same expression system (i.e. pHP13 with the mdh promoter) in shake flasks (Table 5). Based on the overall results obtained for single genes, we have constructed vectors with coupled overexpression of two or more genes using the same expression system, and demonstrated additive effects on L-lysine production levels in MGA3 (see Table 5).

TABLE 4

L-lysine production yields (mg/l) obtained in shake flask cultures of recombinant *B. methanolicus* strain MGA3 growing on methanol.

| Vector | promoter | L-lysine yield (mg/l) |
|---|---|---|
| pHP13 | No | 6 |
| pHP13mp-dapG | mdhP | 7 |
| pHP13mp-lysC | mdhP | 55 |
| pHP13mp-yclM | mdhP | 110 |
| pTH1mp-dapA | mdhP | 7 |
| pTH1mp-asd | mdhP | 7 |
| pTH1mp-lysA | mdhP | 150 |
| pTH1mp-dapA + yclM | mdhP | 250 |
| pTH1mp-yclM + lysA | mdhP | 220 |
| pTH1mp-yclM + lysA + dapA | mdhP | 310 |

Comments to Table 4:
  All expressed genes are described in FIG. 1 and vector constructions are given in Materials and Methods
  For all recombinant genes transcription is driven by the mdh promoter (mdhP)
  All recombinant genes are under translational control of the mdh ribosome binding site
  Production yields in shake flasks are much lower compared to when strains are tested in fermentors; however, the relative effects are comparable.

These data show, as in Example 1, that overexpression of yclM results in much higher L-lysine production than seen with AKI (dapG) and AKII (lysC) genes. It is further shown that an improved effect on lysine production may be obtained by combining AKIII overexpression with overexpression of other genes of the lysine biosynthetic pathway such as dapA (encoding dihydropicolinate synthase) and lysA (encoding meso-dimainopimelate decarboxylase).

EXAMPLE 3

L-Lysine Production on Sugar-Based Growth Media

We have tested recombinant strains described in Example 3 for L-lysine production upon growth in mannitol medium, e.g. strain MGA3 (pTH1mp-lysA) overexpressing lysA, and the results clearly show that the production levels are similar or even higher under these conditions compared to the analogous data obtained in methanol medium (see Table 5). The composition of the mannitol and the methanol media are identical, besides of the C-source.

TABLE 5

L-lysine production yields in shake flask cultures of recombinant *B. methanolicus* strains, upon growth in methanol versus mannitol medium

| | L-lysine yield (mg/l) | |
|---|---|---|
| Overexpressed gene | Methanol (MeOH$_{200}$) | Mannitol (Mann$_{20}$) |
| MGA3 (pHP13) | 6 | 9 |
| MGA3 (pTH1mp-lysA) | 150 | 400 |

Comments to the Growth Media Used:
  MeOH$_{200}$: As described in Jakobsen et al., 2006 (supra)
  Mann$_{20}$: Equal to 2× Mann$_{10}$ as described in Jakobsen et al., 2006 (supra).

The invention claimed is:

1. A method for producing L-lysine in *B. methanolicus*, said method comprising introducing into said *B. methanolicus* a nucleic acid molecule comprising a nucleotide sequence encoding an AKIII enzyme, such that an AKIII enzyme is overexpressed, wherein said nucleotide sequence
   (i) corresponds to a nucleotide sequence as set forth in SEQ ID NO: 3 or a nucleotide sequence having at least 90% identity to SEQ ID NO: 3; or
   (ii) encodes the amino acid sequence as shown in SEQ ID NO: 4 or an amino acid sequence which has at least 90% sequence identity with the amino acid sequence of SEQ ID NO: 4.

2. The method of claim 1 wherein the AKIII is sensitive to feedback inhibition.

3. The method of claim 1 wherein the AKIII is resistant to feedback inhibition.

4. The method of claim 1 wherein the *B. methanolicus* is a wild-type *B. methanolicus*.

5. The method of claim 1 wherein the *B. methanolicus* is an auxotroph or a mutant resistant to a lysine analogue.

6. The method of claim 1 wherein the AKIII is overexpressed in combination with the expression or overexpression of other genes in the microorganism.

7. The method of claim 1 wherein the nucleic acid molecule comprising a nucleotide sequence encoding an AKIII is expressed from a non-native promoter.

8. The method of claim 7 wherein the promoter is a strong promoter.

9. The method of claim 1 wherein the expression of the nucleotide sequence is not subject to transcriptional repression.

10. A *B. methanolicus* microorganism which overexpresses an AKIII enzyme wherein said *B. methanolicus* has been genetically modified by introducing a nucleic acid molecule comprising a nucleotide sequence encoding an AKIII enzyme, wherein said nucleotide sequence
    (i) corresponds to a nucleotide sequence as set forth in SEQ ID NO: 3 or a nucleotide sequence having at least 90% identity to SEQ ID NO: 3; or
    (ii) encodes the amino acid sequence as shown in SEQ ID NO: 4 or an amino acid sequence which has at least 90% sequence identity with the amino acid sequence of SEQ ID NO: 4.

11. The microorganism of claim 10 wherein the AKIII is sensitive to feedback inhibition.

12. The microorganism of claim 10 wherein the AKIII is resistant to feedback inhibition.

13. The microorganism of claim 10 wherein the microorganism is a genetically modified wild-type *B. methanolicus*.

14. The microorganism of claim 10 wherein the microorganism is an auxotroph or a mutant resistant to a lysine analogue.

15. The microorganism of claim 10 wherein the AKIII is overexpressed in combination with the expression or overexpression of other genes in the microorganism.

16. The microorganism of claim 10 wherein the nucleic acid molecule comprising a nucleotide sequence encoding an AKIII is expressed from a non-native promoter.

17. The microorganism of claim 16 wherein the promoter is a strong promoter.

18. The microorganism of claim 10 wherein the expression of the nucleotide sequence is not subject to transcriptional repression.

19. A synthetic nucleic acid molecule, which encodes a polypeptide having AK activity, comprising or consisting of a nucleotide sequence selected from the group consisting of:
  (i) a nucleotide sequence as set forth in SEQ ID NO: 3,
  (ii) a nucleotide sequence having at least 90% sequence identity with a nucleotide sequence as set forth in SEQ ID NO: 3,
  (iii) a nucleotide sequence encoding the polypeptide whose amino acid sequence is set forth in SEQ ID NO: 4; and
  (iv) a nucleotide sequence encoding a polypeptide which has an amino acid sequence having at least 90% sequence identity with an amino acid sequence as set forth in SEQ ID NO: 4.

20. An isolated polypeptide having AK activity and comprising or consisting of a sequence of amino acids selected from the group consisting of:
  (i) an amino acid sequence as set forth in SEQ ID NO: 4, and
  (ii) an amino acid sequence having at least 90% sequence identity with an amino acid sequence as set forth in SEQ ID NO: 4.

21. A construct comprising a nucleic acid molecule which encodes a polypeptide having AK activity, comprising or consisting of a nucleotide sequence selected from the group consisting of:
  (i) a nucleotide sequence as set forth in SEQ ID NO: 3,
  (ii) a nucleotide sequence having at least 90% sequence identity with a nucleotide sequence as set forth in SEQ ID NO: 3,
  (iii) a nucleotide sequence encoding the polypeptide whose amino acid sequence is set forth in SEQ ID NO: 4; and
  (iv) a nucleotide sequence encoding a polypeptide which has an amino acid sequence having at least 90% sequence identity with an amino acid sequence as set forth in SEQ ID NO: 4,
  said nucleic acid molecule encoding an AKIII enzyme, operably linked to a non-native promoter.

22. A vector comprising a nucleic acid molecule which encodes a polypeptide having AK activity, comprising or consisting of a nucleotide sequence selected from the group consisting of:
  (i) a nucleotide sequence as set forth in SEQ ID NO: 3,
  (ii) a nucleotide sequence having at least 90% sequence identity with a nucleotide sequence as set forth in SEQ ID NO: 3,
  (iii) a nucleotide sequence encoding the polypeptide whose amino acid sequence is set forth in SEQ ID NO: 4; and
  (iv) a nucleotide sequence encoding a polypeptide which has an amino acid sequence having at least 90% sequence identity with an amino acid sequence as set forth in SEQ ID NO: 4.

23. A vector comprising a construct as defined in claim 21.

24. A host microorganism into which a nucleic acid molecule which encodes a polypeptide having AK activity, comprising or consisting of a nucleotide sequence selected from the group consisting of:
  (i) a nucleotide sequence as set forth in SEQ ID NO: 3,
  (ii) a nucleotide sequence having at least 90% sequence identity with a nucleotide sequence as set forth in SEQ ID NO: 3,
  (iii) a nucleotide sequence encoding the polypeptide whose amino acid sequence is set forth in SEQ ID NO: 4; and
  (iv) a nucleotide sequence encoding a polypeptide which has an amino acid sequence having at least 90% sequence identity with an amino acid sequence as set forth in SEQ ID NO: 4,
  has been introduced.

25. A host microorganism into which a construct as defined in claim 21 has been introduced.

26. A host microorganism into which a vector as defined in claim 22 has been introduced.

27. A host microorganism into which a vector as defined in claim 23 has been introduced.

28. The microorganism of claim 10 wherein said nucleotide sequence encoding said AKIII enzyme is obtainable from a *Bacillus* sp.

29. The microorganism of claim 28 wherein said nucleotide sequence encoding said AKIII enzyme is obtainable from a *Bacillus* sp. selected from *B. subtilis*, *B. licheniformis*, *B. halodurans*, and *B. amyloliquefaciens*.

30. The micororganism of claim 10 wherein said nucleotide sequence encoding said AKIII enzyme is a variant of SEQ ID NO: 3 wherein the variation is a nucleotide addition, substitution, insertion or deletion relative to SEQ ID NO: 3.

31. The microorganism of claim 30 wherein said nucleotide sequence encoding said AKIII enzyme has 1, 2, 3, 4 or 5 or more nucleotide additions, substitutions, insertions or deletions.

* * * * *